US010768093B2

(12) United States Patent
Friedersdorf et al.

(10) Patent No.: US 10,768,093 B2
(45) Date of Patent: Sep. 8, 2020

(54) MEASUREMENT SYSTEMS AND METHODS FOR CORROSION TESTING OF COATINGS AND MATERIALS

(71) Applicant: Luna Innovations Incorporated, Roanoke, VA (US)

(72) Inventors: Fritz John Friedersdorf, Earlysville, VA (US); Conrad Koenig Andrews, Charlottesville, VA (US); Paul Gordon Muskopf, Charlottesville, VA (US); Kathryn Beryl Ridder, Pittsburgh, PA (US)

(73) Assignee: Luna Innovations Incorporated, Roanoke, VA (US)

( * ) Notice: Subject to any disclaimer, the term of this patent is extended or adjusted under 35 U.S.C. 154(b) by 379 days.

(21) Appl. No.: 15/480,609

(22) Filed: Apr. 6, 2017

(65) Prior Publication Data
US 2017/0205333 A1 Jul. 20, 2017

Related U.S. Application Data

(62) Division of application No. 14/496,164, filed on Sep. 25, 2014.
(Continued)

(51) Int. Cl.
*G01N 17/02* (2006.01)
*G01N 17/04* (2006.01)
(Continued)

(52) U.S. Cl.
CPC ............... *G01N 17/04* (2013.01); *G01N 3/02* (2013.01); *G01N 3/06* (2013.01); *G01N 17/02* (2013.01);
(Continued)

(58) Field of Classification Search
CPC ........ G01N 17/043; G01N 17/04; G01N 17/02
(Continued)

(56) References Cited

U.S. PATENT DOCUMENTS 4,780,664 A * 10/1988 Ansuini ................. G01N 17/00
204/404
4,994,159 A 2/1991 Agarwala et al.
(Continued)

OTHER PUBLICATIONS

Office Action dated May 31, 2018 in co-pending U.S. Appl. No. 14/496,164, 6 pages.
(Continued)

*Primary Examiner* — Melissa J Koval
*Assistant Examiner* — Courtney G McDonnough
(74) *Attorney, Agent, or Firm* — Nixon & Vanderhye P.C.

(57) ABSTRACT

A measurement system permits environmental, corrosion damage, and mechanical property measurements to assess protection properties of coatings. The system includes one or more multi-sensor panels, each multi-sensor panel having sensors for assessing coating barrier properties, free corrosion, and galvanic corrosion. Each multi-sensor panel is installed on a test rack that contains electronics for sensor excitation and sensor data acquisition throughout a corrosion test. Sensor data is collected, stored, and communicated to a base station. A network of multiple test racks can be supported by a base station to compare the performance of different coatings and material combinations simultaneously. The test racks can be used in accelerated atmospheric corrosion tests, outdoor test sites, or application service environments. Measurements of the capacity of a coating to maintain barrier properties, prevent free corrosion, galvanic corrosion, and environment-assisted cracking can be used to develop, select, and predict service performance of coatings.

21 Claims, 13 Drawing Sheets

Related U.S. Application Data

(60) Provisional application No. 61/883,648, filed on Sep. 27, 2013.

(51) Int. Cl.
| | | |
|---|---|---|
| G01N 3/02 | (2006.01) | |
| G01N 3/06 | (2006.01) | |
| G01N 27/02 | (2006.01) | |
| G01N 27/04 | (2006.01) | |
| G01N 27/20 | (2006.01) | |
| G01N 27/22 | (2006.01) | |
| G01N 33/00 | (2006.01) | |
| G01N 3/20 | (2006.01) | |
| G01N 19/04 | (2006.01) | |
| G01N 3/08 | (2006.01) | |

(52) U.S. Cl.
CPC .......... *G01N 17/043* (2013.01); *G01N 27/023* (2013.01); *G01N 27/041* (2013.01); *G01N 27/20* (2013.01); *G01N 27/22* (2013.01); *G01N 33/0031* (2013.01); *G01N 3/08* (2013.01); *G01N 3/20* (2013.01); *G01N 19/04* (2013.01); *G01N 2203/024* (2013.01)

(58) Field of Classification Search
USPC .......................................................... 324/522
See application file for complete search history.

(56) References Cited

U.S. PATENT DOCUMENTS

| | | | |
|---|---|---|---|
| 5,338,432 A | 8/1994 | Agarwala et al. | |
| 5,859,537 A | 1/1999 | Davis et al. | |
| 6,623,616 B1 | 9/2003 | Malver | |
| 6,894,512 B2 | 5/2005 | Girshovich et al. | |
| 6,911,828 B1 * | 6/2005 | Brossia .................. | G01N 17/02 324/649 |
| 6,952,095 B1 | 10/2005 | Goldfine et al. | |
| 7,313,947 B2 | 1/2008 | Harris et al. | |
| 7,477,060 B2 | 1/2009 | Yu et al. | |
| 7,678,260 B1 * | 3/2010 | Yang ...................... | G01N 17/02 204/404 |
| 7,877,009 B2 | 1/2011 | Wang et al. | |
| 8,085,165 B2 | 12/2011 | Wavering et al. | |
| 9,518,915 B2 | 12/2016 | Friedersdorf et al. | |
| 2006/0162431 A1 * | 7/2006 | Harris .................. | G01N 17/006 73/86 |
| 2007/0144272 A1 * | 6/2007 | Yu ......................... | G01N 17/02 73/862.046 |
| 2007/0193887 A1 | 8/2007 | Tormoen et al. | |
| 2008/0141780 A1 | 6/2008 | Wavering et al. | |
| 2008/0150555 A1 | 6/2008 | Wang et al. | |
| 2008/0204275 A1 * | 8/2008 | Wavering ............... | G01N 17/04 340/870.16 |
| 2010/0132469 A1 * | 6/2010 | Giurgiutiu ........... | G01N 29/245 73/628 |
| 2010/0133120 A1 * | 6/2010 | Varney ................. | G01N 33/497 205/785.5 |
| 2011/0012628 A1 | 1/2011 | Dobashi | |
| 2011/0210014 A1 | 9/2011 | Garosshen | |
| 2012/0038377 A1 | 2/2012 | Hamann | |
| 2012/0081136 A1 | 4/2012 | Davis et al. | |
| 2013/0069676 A1 * | 3/2013 | Steinwandel .......... | G01R 27/02 324/700 |
| 2013/0098151 A1 * | 4/2013 | Sulaiman .............. | G01N 27/225 73/335.04 |
| 2013/0265064 A1 | 10/2013 | Hamann | |
| 2015/0268152 A1 | 9/2015 | Friedersdorf | |
| 2016/0041085 A1 | 2/2016 | England | |

OTHER PUBLICATIONS

U.S. Appl. No. 14/496,164, filed Sep. 25, 2014, Inventor: Friedersdorf et al.

Office Action dated Apr. 5, 2017 in co-pending U.S. Appl. No. 14/496,164, 9 pages.

International Search Report for PCT/US2013/050424, dated Oct. 14, 2013, 2 pages.

Demo, et al., "Wireless Corrosion Monitoring for Evaluation of Aircraft Structural Health", 2012 IEEE Aerospace Conference, pp. 1-10, (Mar. 10, 2012).

Demo et al., "Diagnostics and Prognostics for Aircraft Structures Using a Wireless Corrosion Monitoring Network", 2011 IEEE Aerospace Conference, pp. 1-10, (Mar. 5-12, 2011).

Demo et al., "Development of a Wireless Miniaturized Smart Sensor Network for Aircraft Corrosion Monitoring", 2010 IEEE Aerospace Conference (IEEEAC paper #1107, Version 3, updated Dec. 22, 2009) pp. 1-9, Mar. 13, 2010.

I.S. Cole et al, "A Sensor-Based Learning Approach to Prognostics in Intelligent Vehicle Health Monitoring" *Materials Forum*, vol. 33, 2009, [in Proceedings of the 2nd Asia-Pacific workshop on structural health monitoring (2APWSHM), Melbourne, Dec. 2008] pp. 27-35.

I.S. Cole et al, "Development of a Sensor-Based Learning Approach to Prognostics in Intelligent Vehicle Health Monitoring" *2008 International Conference on Prognostics and Health Management*, Oct. 6-9, 2008, 7 pages.

International Preliminary Report on Patentability dated Feb. 5, 2015 in PCT/US2013/050424, 7 pages.

R. Summitt et al, "Pacer Lime: Part II—Experimental Determination of Environmental Corrosion Severity" Jun. 1980, at http://www.dtic.mil/docs/citations/ADA108552, 35 pages.

S. Morefield et al, "Development of Predictive Corrosion Model Using Locality-Specific Corrosion Indices" US Army Corps of Engineers, DoD Corrosion Prevention and Control Program, ERDC/CERL TR-09-22, Aug. 2009, 90 pages.

T. Trueman et al, "The development of a corrosion prognostic health management system for Australian Defence Force aircraft" *Advanced Materials Research*, vol. 38 (2008), Mar. 2008, pp. 182-200.

V.S. Agarwala et al, "Corrosion Detection and Monitoring—A Review" *Corrosion 2000*, Paper No. 00271, Mar. 2000, 19 pages.

Office Action dated Nov. 3, 2017 in co-pending U.S. Appl. No. 14/496,164, 7 pages.

Final Office Action dated Dec. 31, 2018 in co-pending U.S. Appl. No. 14/496,164, 7 pages.

Office Action dated Jun. 13, 2019 in co-pending U.S. Appl. No. 14/496,164, 9 pages.

Advisory Action dated May 3, 2019 in co-pending U.S. Appl. No. 14/496,164, 4 pages.

Final Office Action dated Jan. 24, 2020 in co-pending U.S. Appl. No. 14/496,164, 10 pages.

* cited by examiner

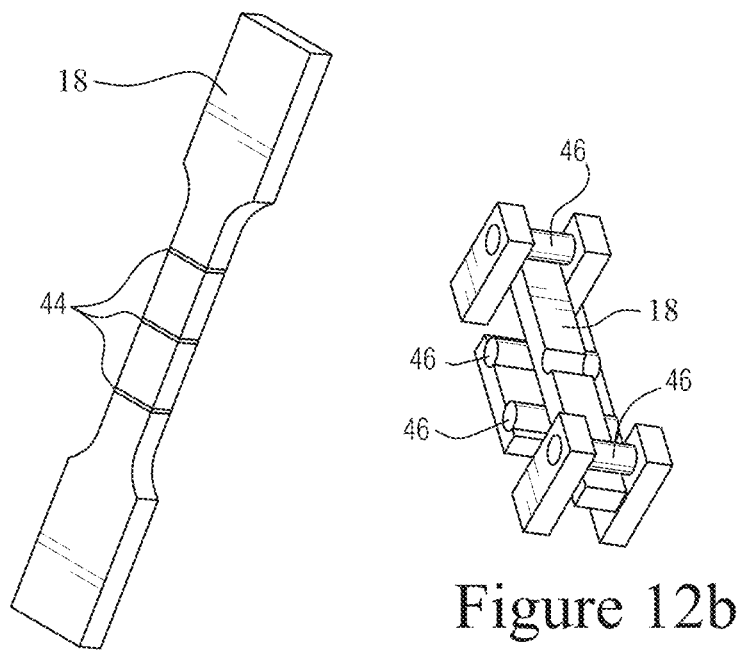
Figure 12a
Figure 12b
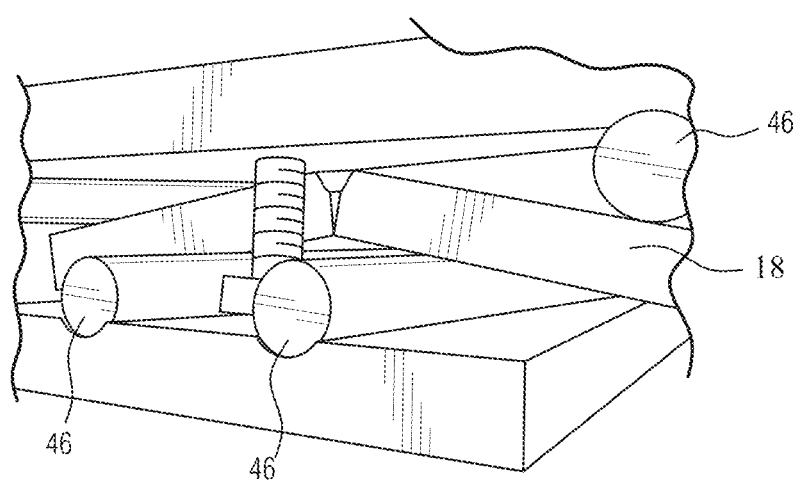
Figure 12c

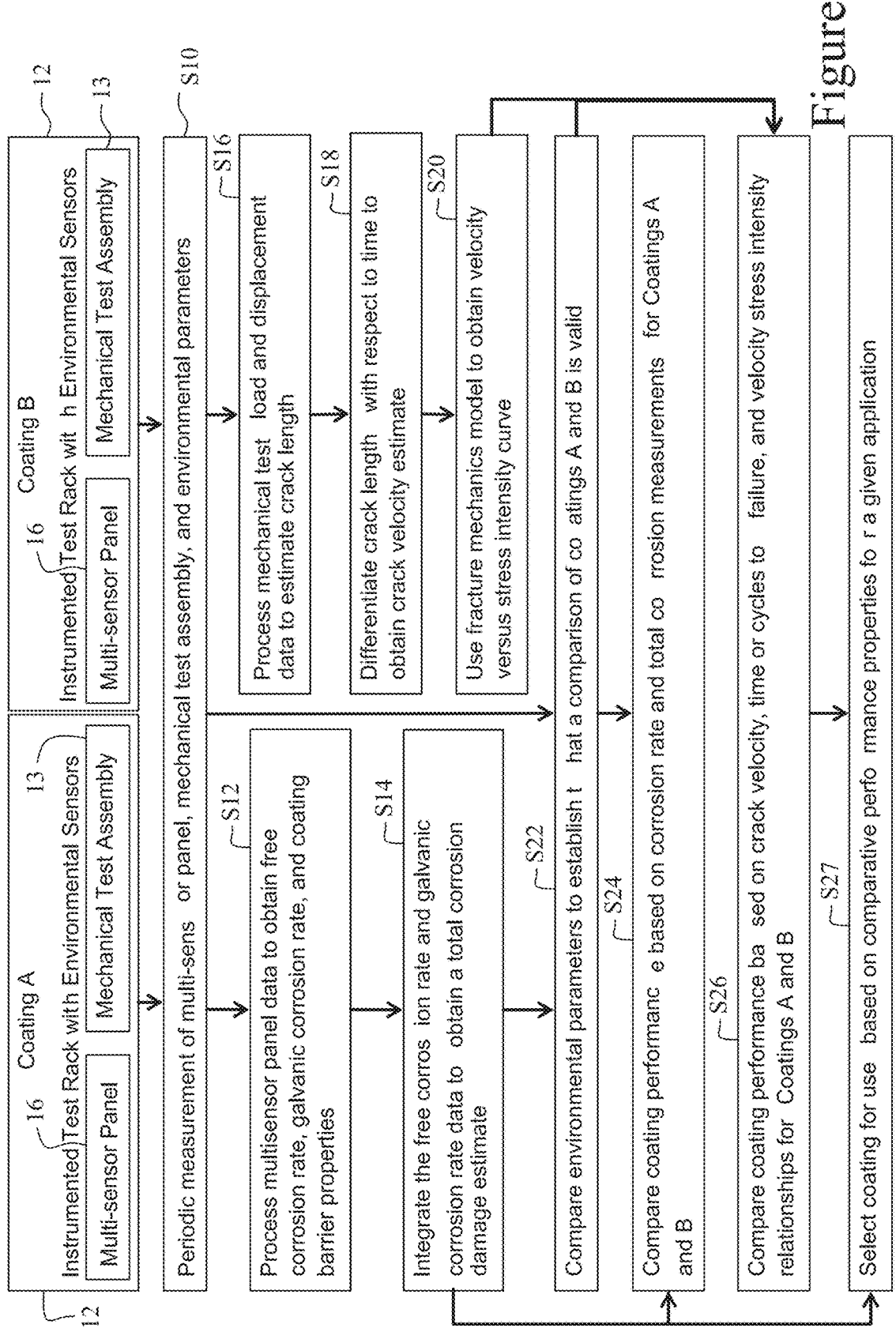

MEASUREMENT SYSTEMS AND METHODS FOR CORROSION TESTING OF COATINGS AND MATERIALS

PRIORITY APPLICATION

This application is a divisional of U.S. patent application Ser. No. 14/496,164, filed Sep. 25, 2014, which claims priority from U.S. provisional patent application No. 61/883,648, filed on Sep. 27, 2013, the contents of each of which are incorporated herein by reference.

Related PCT Application

Reference is made to PCT application No. PCT/US2013/050424, claiming priority to U.S. provisional application No. 61/675,996, entitled "Sensing Systems and Methods for Determining and Classifying Corrosivity," the entire contents of which are incorporated herein by reference.

GOVERNMENT RIGHTS

This invention was made with Government support under Contract No. FA9501-12-P-0097 awarded by the U.S. Air Force. The Government has certain rights to the invention.

FIELD

The example embodiments described below relate to systems and methods for coating and material property testing.

BACKGROUND

A coating or coating system may include cleaning, pretreatment, and multiple organic coating layers such as primer, topcoat, and clear coat. Multiple processing steps and coating layers may be employed to form a coating system.

The annual cost of corrosion to the US economy was estimated to be $276 billion in 2002. Besides these costs, corrosion also adversely impacts safety and efficiency in a number of economic sectors such as transportation and infrastructure. Corrosion control may be achieved through material and coating selection based on accelerated laboratory corrosion and service environment testing.

Government, military, and industrial performance requirements for materials qualification often rely on pass/fail measurements of scribed flat panels exposed for a given duration in aggressive environments. However, in operational environments, alloys may fail due to other corrosion processes associated with localized corrosion, galvanic couples, and mechanical loading that may not be evaluated using current practices. Known measurement approaches do not include processes and measurements that assess coating protection properties for atmospheric corrosion that can lead to subsequent generation of environment-assisted cracking, corrosion fatigue, and fatigue.

Thus, there is a need to improve coatings and materials corrosion testing. One way to do this, recognized by the inventors, is to leverage advances in sensing and instrumentation to obtain high fidelity data on corrosion performance and degradation processes. A reliable measurement system that improves the corrosion evaluation of coatings on structural materials would be useful for example for: coating development and improvement, coating and materials selection to achieve design life and warrantee performance for specific service environments, and comparative testing for optimal coating and materials selection.

To minimize risk associated with the introduction of new materials (alloys and coatings), most industries use a staged approach for product evaluation and qualification that includes a series of laboratory studies, outdoor exposure site tests, and limited use service trials. In the specific case of a new coating, full qualification usually takes a minimum of three years to achieve acceptance and often this can take much longer. The lengthy qualification process is due to the nature and variety of degradation processes being evaluated, uncertainty in test results, and coarse performance measurements.

Current military coating evaluation and qualification methods for aircraft pretreatments, primers, and full coating systems rely on salt fog testing of scribe panels according to ASTM B117. The salt fog test is a relatively simple chamber test developed in the 1950s where components or samples are exposed to constant conditions of humidity, temperature, and salt spray. It is widely accepted that salt fog testing is most appropriate for quality assurance purposes, and efforts have been made to establish more sophisticated cyclic testing like ASTM G85 to achieve conditions that are similar to those that occur in operational environments such as for automotive products and to better simulate acidic or industrial environments.

Commonly coating performance specifications require the use of flat test coupons with scribes through the paint to the bare metal (ASTM D1654, MIL-PRF-32239, ASTM G1). In general, to meet coating performance requirements there should be no blistering, lifting, or substrate pitting, and in the case of chromate primers, no corrosion in the scribe (see, e.g., MIL-PRF-32239). Although there have been efforts to establish more realistic test panels that better approximate the components of interest, and refine methods to quantify corrosion damage, currently prescribed tests tend to be pass/fail evaluations and do not provide a rank order of performance nor any time-based information related to precursor, incubation, and growth processes of damage state progression for the various mechanisms that may be occurring.

Corrosion test practices rely heavily on operator visual or optical inspections and rating criteria that are applied at the conclusion of an accelerated test or outdoor exposure (ASTM 1654). Little to no information on the corrosion kinetics is obtained, and often knowledge of the impact of galvanic processes and the effect of localized corrosion on residual strength or environment-assisted cracking is not determined. The measurement time, uncertainty, and limited mechanistic information make it difficult to assess relative performance for product acceptance and qualification, ultimately slowing coating product development and product integration.

Furthermore, often the properties being evaluated using previous methods do not measure the damage modes or mechanisms that are relevant to the specific application. Specifically, free corrosion of the alloy or blistering of the paint film may be less important than galvanic corrosion, protection against pitting, and resulting loss of strength of the structural component. Finally, since little information on the corrosion rate or rate of change of corrosion can be elucidated, the rank order performance of materials is dependent on the test period, and significant risk exists for choosing a material with poor long-term performance.

In order to obtain the maximum benefit from sophisticated test protocols and automated accelerated corrosion test chambers, improved in situ measurements of the progression of coating system breakdown and the various forms of corrosion that are relevant to a particular use or application are needed. Prior sensor research has focused on either measuring environment or corrosion in outdoor service environments using sensors that measure only limited corrosion processes.

Accordingly, there is a significant need for an improved measurement system for judging the multiple dynamic processes associated with corrosion and coating performance to achieve a more complete solution set for coating and materials development and qualification.

SUMMARY

Example embodiments relate to a system for measuring time varying processes of atmospheric corrosion. The system includes a test rack holding a sensor panel including one or more sensors configured to measure one or more protective properties of a coating applied to the sensor panel, and circuitry configured to obtain measurement information from the one or more sensors on the sensor panel and to evaluate the one or more protective properties of the coating. For example, the one or more protective properties indicate an effectiveness of the coating in preventing corrosion that attacks an underlying substrate upon which the coating is provided. Specific example protective properties include one or more of: a barrier property of the coating, a protection of an underlying substrate upon which the coating is provided from free corrosion, or a protection of the substrate from galvanic corrosion. Example applications for the system include obtaining atmospheric corrosion information from a laboratory test chamber, an outdoor exposure site, or an application service location.

In further example embodiments, the test rack also holds a standard coating test panel and/or one or more environmental sensors configured to provide environmental sensor information including one or more of measured relative humidity, air temperature, surface temperature, and conductivity parameters. The one or more environmental sensors may be configured to provide environmental sensor information based on measured anions, cations, or gases and/or measured visible, infrared, or ultraviolet radiation.

In yet other example embodiments, the test rack also holds one or more mechanical test assemblies, each mechanical test assembly having a mechanical test specimen, a load mechanism configured to apply a load to the mechanical test specimen, and a mechanical test specimen sensor configured to measure mechanical properties. The load mechanism is configured to apply a load to the mechanical test specimen, and the mechanical test specimen sensor is configured to measure environment-assisted crack growth rate in the mechanical test specimen during atmospheric corrosion testing.

The system may include multiple test racks, in which case, the circuitry is configured to obtain measurement information from each of the multiple test racks and to evaluate the sensors on each rack for susceptibility to corrosion based on the obtained measurement information.

The system, in example embodiments, includes communication circuitry configured to communicate measurement information or corrosion susceptibility evaluation information to a base station. In one example, radio communication circuitry is configured to wirelessly communicate measurement information or corrosion susceptibility evaluation information to the base station.

In example embodiments, the test rack holds multiple sensor panels each including one or more sensors configured to measure one or more protective properties of a different coating applied to different ones of the sensor panels. The circuitry is configured to obtain measurement information from the one or more sensors on each of the multiple sensor panels and to evaluate the one or more protective properties of each of the different coatings.

A further aspect of the technology relates to a sensor panel, e.g., insertable in a test rack, for measuring time varying processes of atmospheric corrosion. The panel includes multiple different sensors configured to measure one or more protective properties of a coating applied to the sensor panel. In one embodiment, the sensor panel has at least two sensors from the group of a free corrosion sensor, a galvanic corrosion sensor, and a coating barrier property sensor, and an interface coupled to the sensors and configured to provide measurement signals from the sensors. The measurement signals include information relating to one or more protective properties of the coating. The interface is configured to obtain measurement information from the one or more sensors that is useable to evaluate the one or more protective properties of the coating.

In example embodiments, the at least two sensors includes the free corrosion sensor, and the free corrosion sensor includes interdigitated electrodes. The interdigitated electrodes may be laminated and include a metallographic texture orientation. In addition, The coating may have a known defect of a given geometry. The interdigitated electrodes may also be covered by an inert material to form a crevice to measure free corrosion. The free corrosion sensor may further be configured to measure free corrosion rate using a current response to a predetermined voltage excitation. Integrating the measured free corrosion rate may be performed to estimate cumulative corrosion. Another example is for the free corrosion sensor to be configured to estimate free corrosion using polarization resistance.

In example embodiments, the at least two sensors includes the galvanic corrosion sensor configured to measure galvanic corrosion using two or more electrodes. An area of each of the electrodes exposed to a corrosive atmosphere may be variable. In one example implementation, the electrodes are laminated and include a metallographic texture orientation or a composite laminate orientation. In another example implementation, the coating has a known defect of a given geometry. In yet another example implementation, the interdigitated electrodes are covered by an inert material to form a crevice to measure galvanic corrosion. The galvanic corrosion sensor may be configured to measure a galvanic corrosion rate for each electrode, and a cumulative galvanic corrosion can be estimated by integrating the galvanic corrosion rate.

In example embodiments, the at least two sensors includes the coating barrier property sensor having interdigitated electrodes made using a metal, an alloy, or a noble metal. The coating barrier property sensor is configured to measure barrier properties of a coating based on impedance measurements between electrodes generated by an excitation voltage.

BRIEF DESCRIPTION OF THE DRAWINGS

FIGS. 12a-12c show example mechanical test specimens and loading mechanisms.

FIG. 16 is flowchart diagram illustrating non-limiting example procedures implemented using two more instrumented test racks to evaluate the corrosion and coating performance of two more coating systems.

DETAILED DESCRIPTION

Figure 1:
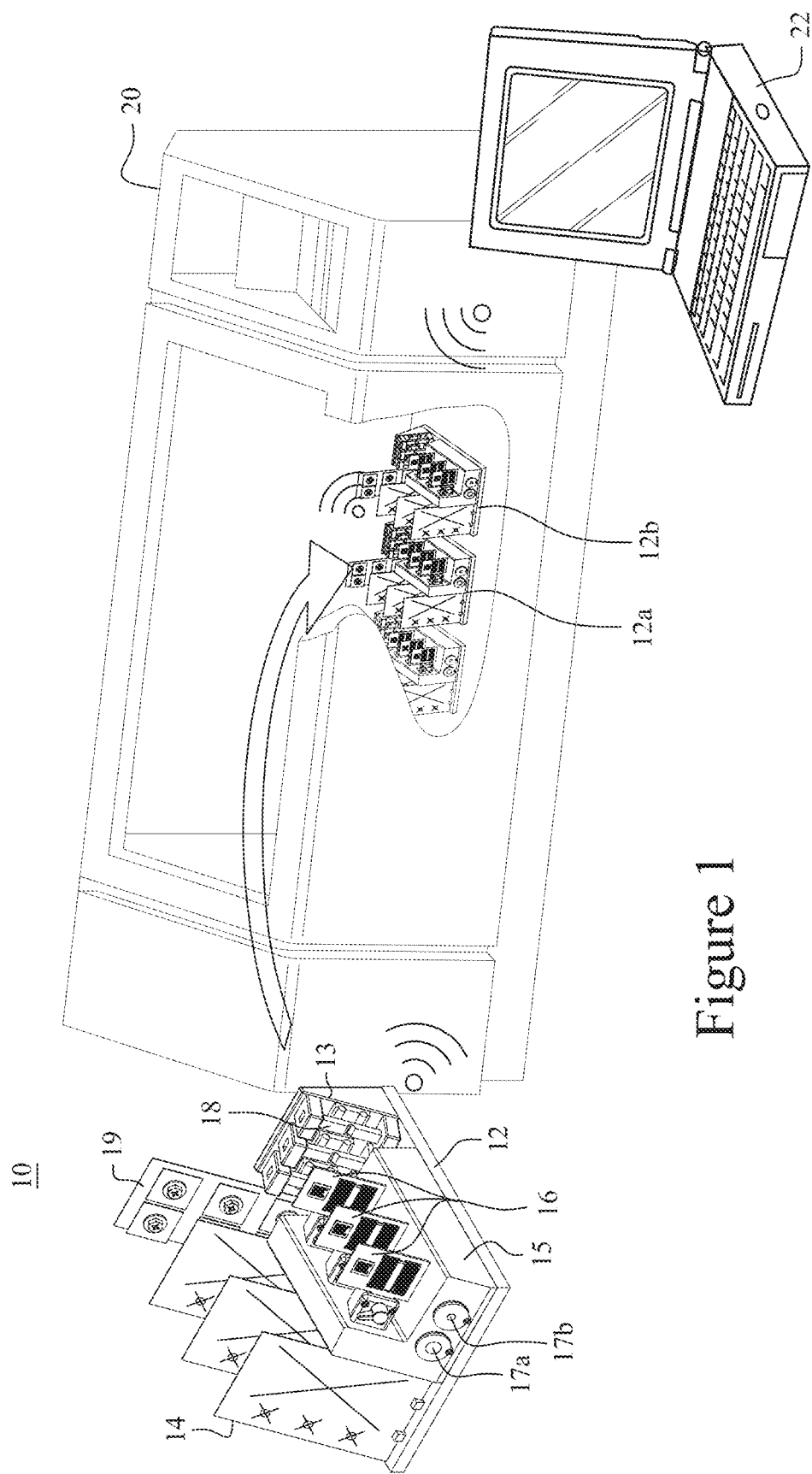
FIG. 1 shows a non-limiting embodiment of a corrosion and coating evaluation system.

The following description sets forth example embodiments for purposes of explanation and not limitation. But it will be appreciated by those skilled in the art that other embodiments may be employed apart from these specific details. In some instances, detailed descriptions of well known methods, interfaces, circuits, and devices are omitted so as not obscure the description with unnecessary detail. Individual blocks are shown in some figures. Those skilled in the art will appreciate that the functions of those blocks may be implemented using individual hardware circuits, using software programs and data in conjunction with a suitably programmed digital microprocessor or general purpose computer, and/or using applications specific integrated circuitry (ASIC), and/or using one or more digital signal processors (DSPs) and/or field programmable gate array(s) (FPGA(s)), and/or (where appropriate) state machines capable of performing such functions. Software program instructions and data may be stored on a non-transitory, computer-readable storage medium, and when the instructions are executed by a computer or other suitable processor control, the computer or processor performs the functions associated with those instructions.

Thus, for example, it will be appreciated by those skilled in the art that diagrams herein can represent conceptual views of illustrative circuitry or other functional units. The functions of various illustrated blocks may be provided through the use of hardware such as circuit hardware and/or hardware capable of executing software in the form of coded instructions stored on computer-readable medium. Thus, such functions and illustrated functional blocks are to be understood as being either hardware-implemented and/or computer-implemented, and thus machine-implemented.

In terms of computer implementation, a computer is generally understood to comprise one or more processors or one or more controllers, and the terms computer, processor, and controller may be employed interchangeably. When provided by a computer, processor, or controller, the functions may be provided by a single dedicated computer or processor or controller, by a single shared computer or processor or controller, or by a plurality of individual computers or processors or controllers, some of which may be shared or distributed. Moreover, the term "processor" or "controller" also refers to other hardware capable of performing such functions and/or executing software, such as the example hardware recited above.

The technology described below provides for advantageous and accelerated coating and material property testing. An example system embodiment incorporates environment, corrosion, and mechanical measurements to obtain corrosion performance data during accelerated atmospheric laboratory tests or outdoor exposure studies. The system can be used to establish the performance of structural materials, material combinations, and coatings for predicting performance, comparative testing of materials, and qualifying coatings and materials for specific uses.

A measurement system permits environmental, corrosion damage, and mechanical property measurements along with more traditional standard corrosion test panels to assess protection properties of coatings. The system includes one or more panels each with multiple sensors for assessing coating barrier properties, free corrosion, and galvanic corrosion for assessing coating protection properties. Using multimodal sensing elements, the mechanisms and kinetics of corrosion processes relevant to structural performance can be measured throughout an atmospheric corrosion test. The multi-sensor panel is installed on a test rack that contains electronics for sensor excitation and data acquisition throughout a corrosion test. Sensor data is collected, stored, and communicated to a base station. A network of multiple test racks can be supported by a single base station to compare the performance of different coatings and material combinations simultaneously. The test racks can be used in accelerated atmospheric corrosion tests, outdoor test sites, or application service environments. The test rack may include a mechanical test assembly for static or dynamic loading of a coated mechanical test specimen throughout the test that can be used to measure environment-assisted cracking or corrosion fatigue. The test rack has provisions for supporting a standard coating test panel. These measurements of the capacity of a coating to maintain barrier properties, prevent free corrosion, galvanic corrosion, and environment-assisted cracking can be used to select coatings and predict service performance.

The instrumented test rack, multi-sensor panel, and mechanical test assembly incorporate components and sensors that are durable and designed for use in aggressive environments. The multi-sensor panel and mechanical test specimens include test and sensing elements that are susceptible to corrosion damage that is relevant to one or more structures, such as for example aircraft. The sensing elements for the free corrosion and galvanic corrosion and the mechanical test specimen expose specific metallurgical texture orientations susceptible to localized corrosion. The galvanic sensor may incorporate any combination of two or more alloys or conductive composite materials. The galvanic sensor may be configured to accommodate a wide range of area ratios to mimic specific component geometries. Furthermore, the free corrosion and galvanic corrosion sensors and fracture sample may be capped to produce crevice conditions that are particularly problematic for structural assemblies. The design of the multi-sensor panel is such that after each test, it can be refinished and used again, or it can be treated as disposable items.

Environmental measurements of temperature and relative humidity can be used to verify that the individual instrumented test racks and multi-sensor panels are exposed to similar conditions and that the conditions are comparable to previous and future tests.

The multi-sensor panel with free corrosion, galvanic corrosion, and barrier property sensors is designed to be handled and processed like a coating test coupon. Standard test coupons, mechanical test specimens, and the multi-sensor panel can all be processed though the same coating processes in preparation for testing.

The technology includes a measurement system and method that can be used to improve the corrosion evaluation of coatings, materials and material combinations for use in engineered structures. The system and method provide for evaluation of the susceptibility of a coated component, structure, or mechanical system to corrosion, especially with regard to corrosion damage that is dependent on the protective properties of the coating and that can degrade by general corrosion, galvanic corrosion, crevice corrosion, intergranular corrosion, exfoliation, pitting or other localized attack including initiation and propagation of stress corrosion cracking, hydrogen embrittlement, or corrosion fatigue cracking. The corrosion and coating evaluation system can be used to characterize coatings in accelerated laboratory, outdoor exposure, or service environment performance testing.

The corrosion and coating evaluation system and method includes environmental, corrosion damage, and mechanical property measurements and may be used in one non-limiting, example embodiment along with a more traditional corrosion standard test panel and weigh loss coupons. These measurements are made using an instrumented test rack that is populated with multi-sensor panels. The sensors are selected and prepared based on the specific materials system, component, or application of interest.

For example, a typical aircraft structure may be composed of steel fasteners and aluminum alloy structural components that are protected by a polymer coating that contains an inhibitor. A paint company or aircraft manufacturer may have alternate coatings that could be applicable to the aircraft. These coatings may be desirable based on performance, environmental compliance, ease of application, and/or reduced cost. Based on this scenario, a plurality of example instrumented test racks, each containing 1) one or more environmental sensors (relative humidity, air temperature, and surface temperature), 2) one or more multisensor panels each with aluminum free corrosion sensor, steel and aluminum galvanic corrosion sensor, and coating barrier property sensor, 3) one or more mechanical test assemblies each with a mechanical test specimen, and 4) one or more standard test panels, may be processed with candidate coatings for comparative testing.

The number of instrumented test racks required for comparative testing may depend on the number of candidate coatings to be evaluated. For a given instrumented test rack and a single coating system, the number of multi-sensor panels, mechanical test specimens, standard test panels, and/or mass loss coupons may depend on a requirement for statistical analysis for characterizing coating performance to given confidence level. In a preferred but example embodiment, the instrumented test rack supports triplicate measurements for a single coating system.

A non-limiting example embodiment of a corrosion and coating evaluation system is shown in FIG. 1 and includes an instrumented test rack 12 with electronics enclosure 15 and standard test panels 14 and mass loss coupons 19, individual environmental sensing elements 17a and 17b, a mechanical test assembly 13 and mechanical test specimens 18, multi-sensor panels 16, and a base station 22 with data acquisition, control system, and user interface. The corrosion and coating evaluation system provides for real-time data acquisition and automated recording of corrosion processes on an extensible number of instrumented test racks (e.g., 12a and 12b are labeled) each containing standard test panels 14, multi-sensor panels 16, environmental sensors 17a and 17b, and mechanical test specimens 18. The instrumented test rack also provides for the use of standard test panels 14, mass loss coupons 19, and mechanical property measurements of mechanical test specimens 18 for evaluation in parallel with the multi-sensor panels 16.

Figure 2:
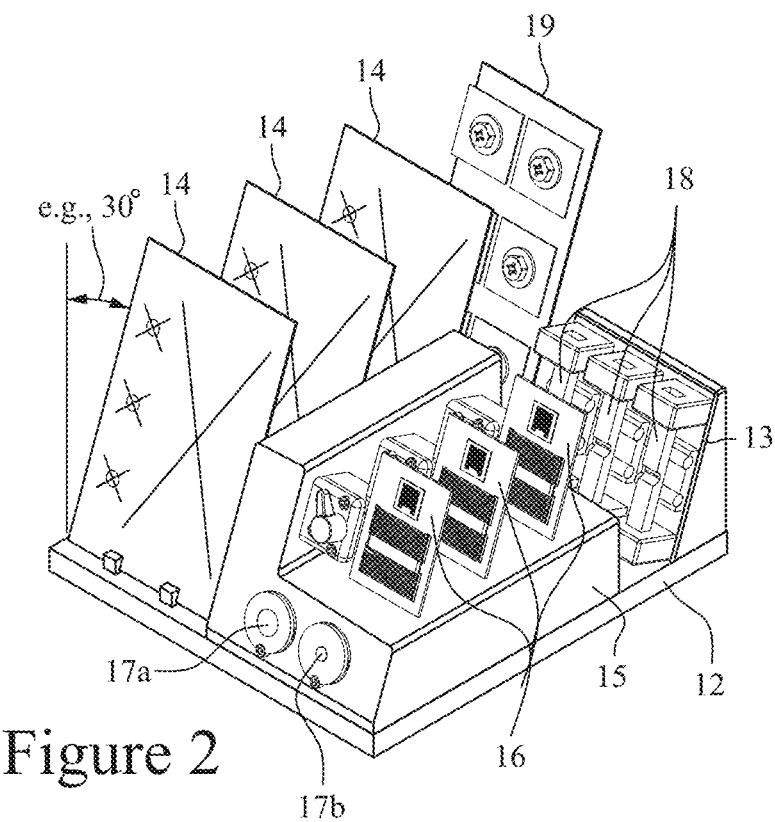
FIG. 2 shows a non-limiting embodiment of an example instrumented test rack with electronics enclosure and a mechanical test assembly.

A single example instrumented test rack 12 in FIG. 2 supports multiple mechanical test specimens 18, multi-sensor panels 16, standard test panels 14, and mass loss coupons 19. A desired number of instrumented test racks are assembled for exposure in an accelerated corrosion test chamber 20. The desired set of instrumented test racks, e.g., 12a and 12b, is put into the corrosion test chamber 20 and the corrosion testing initiated. In one example embodiment, a base station 22 preferably monitors a network of instrumented test racks 12 throughout the test via either a wired or a wireless interface. During testing, the sensing elements for each instrumented test rack record at preset intervals environment, corrosion, and mechanical test specimen load and displacement data. The data is processed to obtain parameters such as corrosion rate, cumulative corrosion, barrier properties, mechanical compliance, and/or crack length parameters throughout the test. At the conclusion of testing, protective properties of tested coatings can be quantified by corrosion rate data, cumulative corrosion damage, barrier properties, and/or fracture mechanics properties. Additional coating performance metrics may be obtained by characterizing the standard test panels 14 and mass loss coupons 18. Environmental measurements 17 of temperature and relative humidity may be used to verify that the individual instrumented test racks 12 were exposed to similar conditions and that the conditions are comparable to previous and future tests and within acceptable bounds for valid testing.

The instrumented test rack data gives a comprehensive assessment of corrosion and coating performance throughout the test. This information can be used to assess damage processes and failure progression for material development studies and comparison of materials for product selection and acceptance.

Besides being useful for comparative testing of materials in standard laboratory accelerated corrosion tests (e.g., ASTM B117, ASTM G85, GM9540P, etc.), the corrosion and coating evaluation system may be used for outdoor corrosion testing and validation of usage assumptions. Instrumented test racks may be used to compare the relative results produced by different environmental conditions, at different geographic locations, or within a structure.

The corrosion and coating evaluation system 10, such as the non-limiting example embodiment shown in FIG. 1, includes: instrumented test racks 12 for atmospheric corrosion testing of coatings technologies that supports multi-modal sensing for continuous assessment of coating barrier properties, various corrosion processes including pitting, intergranular, exfoliation, crevice, galvanic, and environment-assisted cracking mechanisms including corrosion fatigue. The corrosion and coating evaluation system has a configurable modular design for characterizing alloy corrosion, coating performance, and mechanical and fracture properties (compliance, modulus, yield and ultimate tensile strength, cycles to initiation, cycles to failure, crack velocity, threshold stress intensity, and equivalent initial flaw size of material systems). The corrosion and coating test system supports an extensible network of instrumented test racks 12 with wired or wireless multi-drop communications bus.

Figure 3:
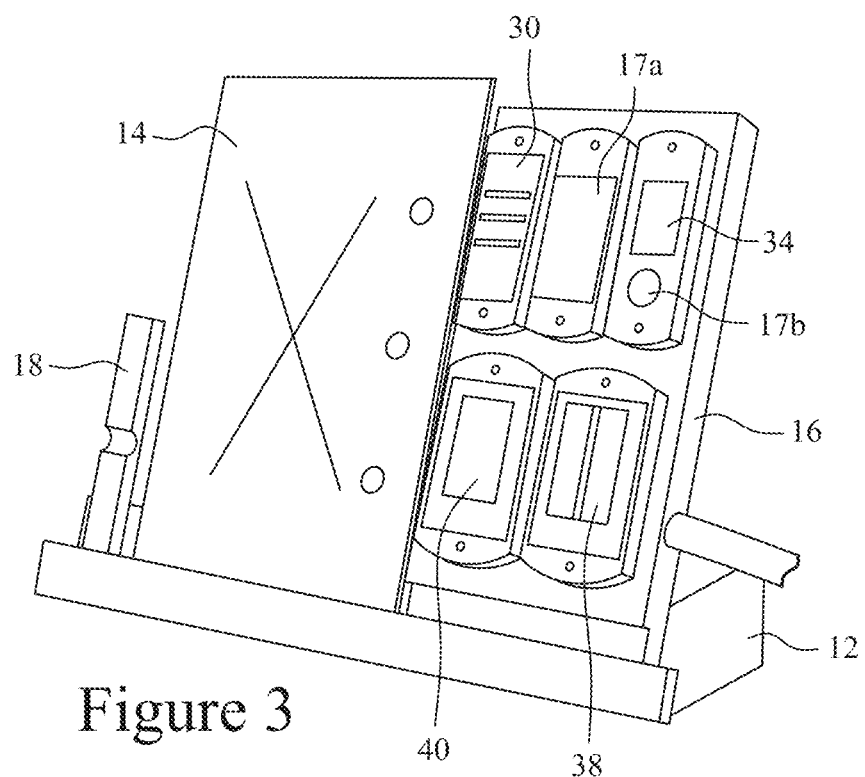
FIG. 3 shows a non-limiting embodiment of an example instrumented test rack with a single standard test panel, mechanical test specimen, and multi-sensor panel where the electronics are remote to the test rack.
Figure 4:
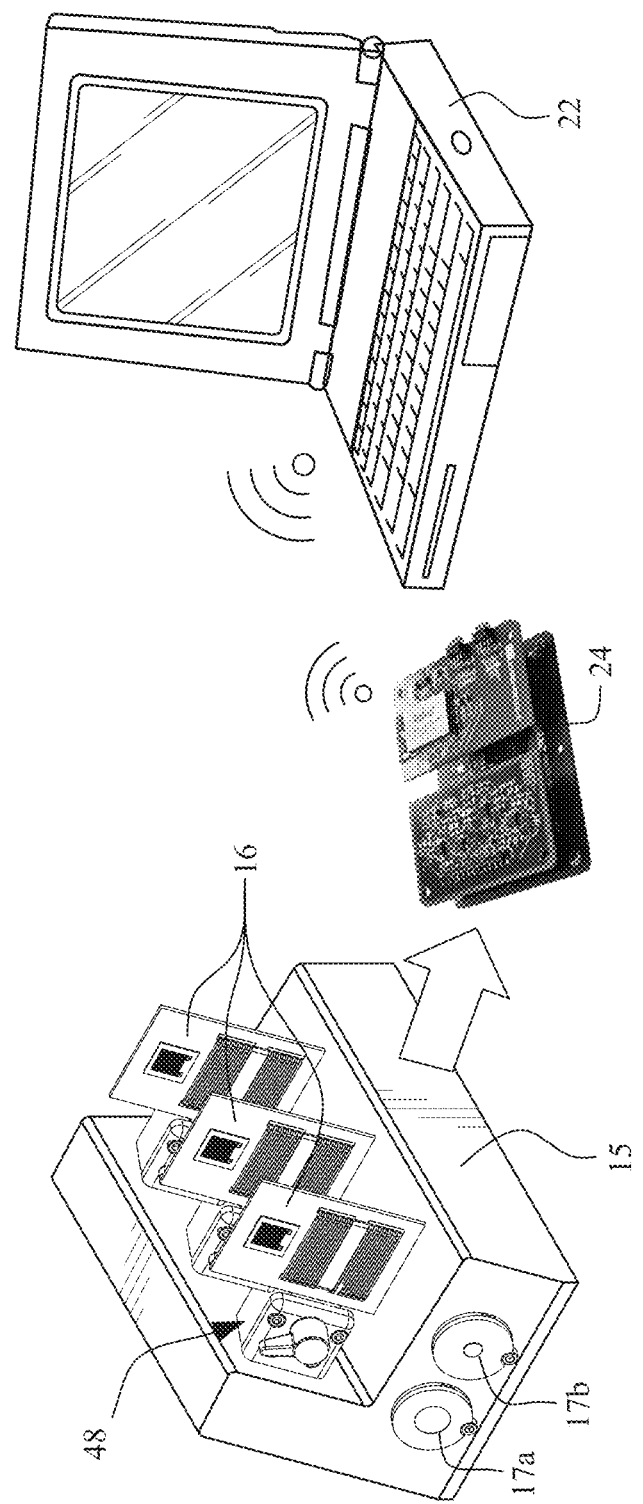
FIG. 4 shows the electronics enclosure of the instrumented test rack similar to that in FIG. 2, a wireless electronics module, and a base station.

The example instrumented test rack 12 shown in FIG. 2 includes an electronics enclosure 15 for physical and electrical interface and data acquisition and control for the multi-sensor panels 16 and mechanical test assembly 13. In a non-limiting example shown in FIG. 4, an electronics module 24 is contained in the electronics enclosure 15 to protect it from the aggressive environment. The electronics module 24 may be controlled by the base station 22 and communicates with the base station 22 by wired or wireless interface as shown in FIG. 4. Alternatively, the acquisition and control electronics of electronics module 24 may be external to the test rack and connect to the multi-sensor panel 16 and test rack 12, e.g., within the chamber, as shown in FIG. 3. The base station 22 communicates with an extensible number of instrumented test racks and preferably supports an intuitive graphical user interface (GUI) and automated menus for test setup, data processing for test configuration, control, and data management.

The system may be used in both controlled laboratory accelerated test chambers 20 and outdoor exposure sites and is capable of long-term, autonomous, real-time, data collection from a large network of instrument test racks 12. The system can continuously measure corrosion processes to obtain quantitative and relative rank order performance based on corrosion rate, cumulative damage, material properties, or fracture and mechanical properties as shown in the example plots illustrated in FIGS. 5-9.

Figure 5:
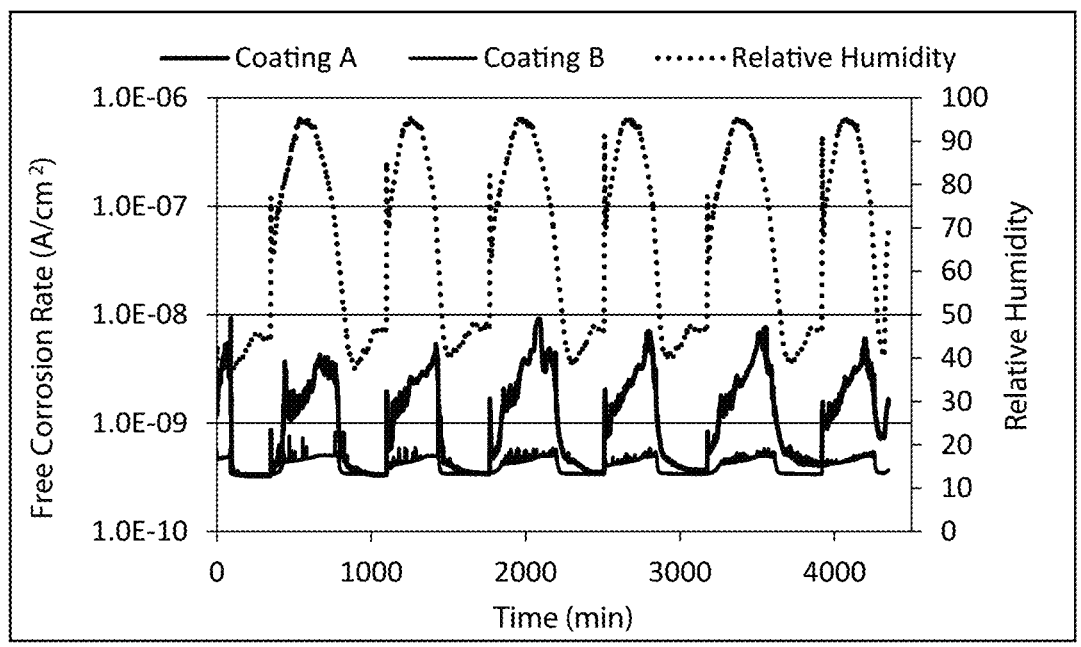
FIG. 5 shows a plot of an example time-based free corrosion rate for two example aluminum alloy free corrosion sensors with coatings tested in an accelerated corrosion test along with a plot of an environmental parameter of relative humidity.

FIG. 5 shows a plot of an example time-based free corrosion rate for two example aluminum alloy free corrosion sensors with coatings tested in an accelerated corrosion test along with a plot of an environmental parameter of relative humidity.

Figure 6:
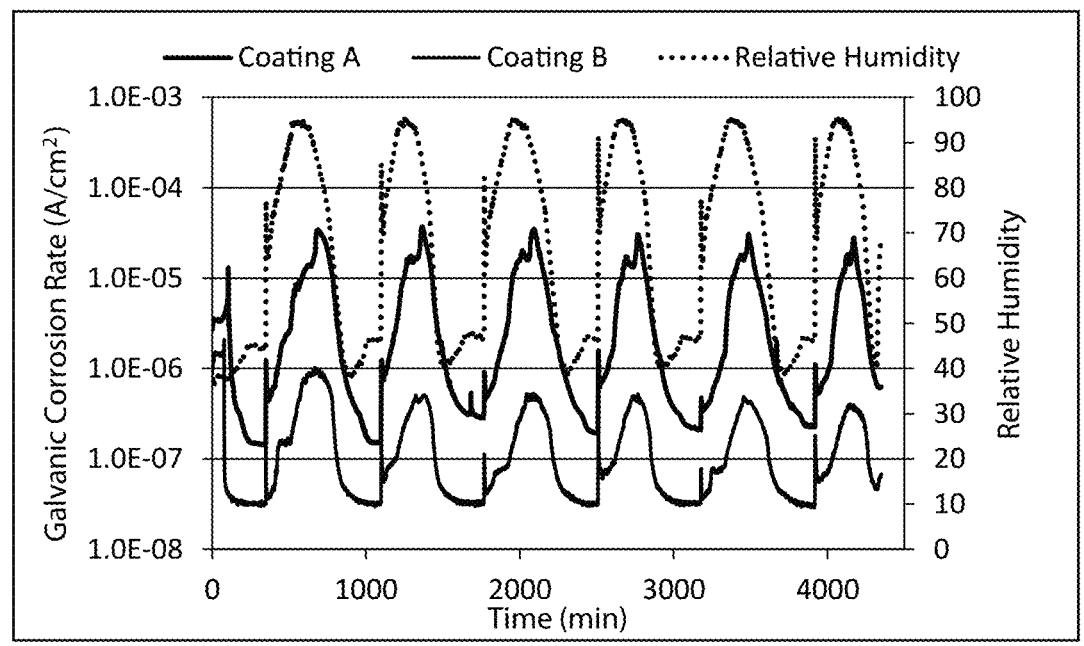
FIG. 6 shows a plot of an example time-based galvanic corrosion rate for example aluminum/copper galvanic corrosion sensors with coatings tested in an accelerated corrosion test along with a plot of an environmental parameter of relative humidity.

FIG. 6 shows a plot of an example time-based galvanic corrosion rate for example aluminum/copper galvanic corrosion sensors with coatings tested in an accelerated corrosion test along with a plot of an environmental parameter of relative humidity.

Figure 7:
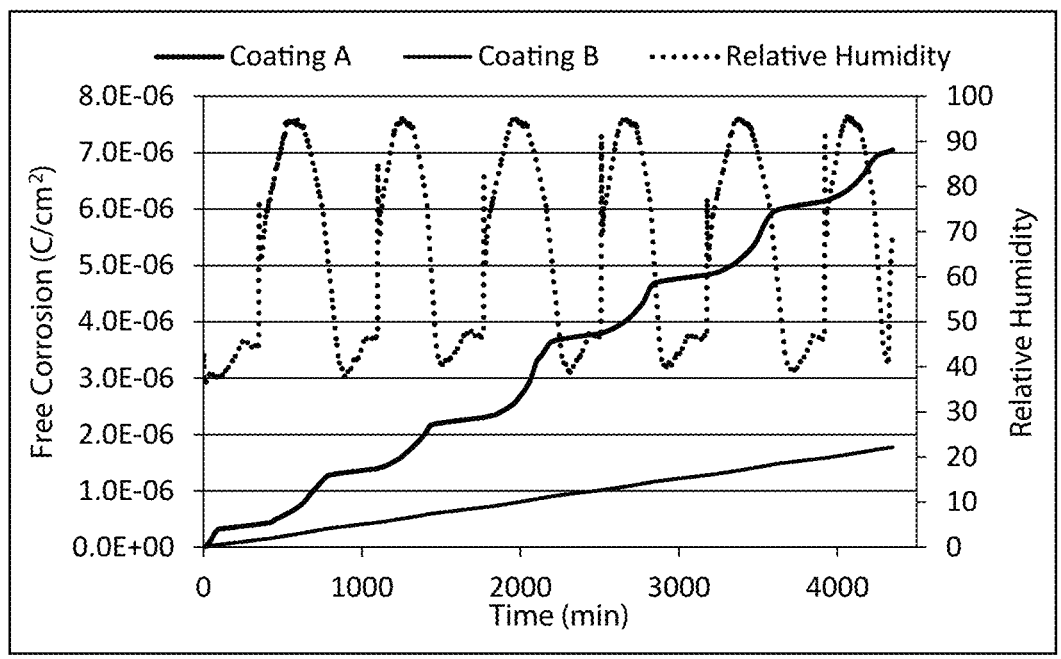
FIG. 7 shows a plot of an example time-based cumulative free corrosion for two aluminum alloy free corrosion sensors with coatings tested in an accelerated corrosion test along with a plot of an environmental parameter of relative humidity.

FIG. 7 shows a plot of an example time-based cumulative free corrosion for two aluminum alloy free corrosion sensors with coatings tested in an accelerated corrosion test along with a plot of a parameter of relative humidity.

Figure 8:
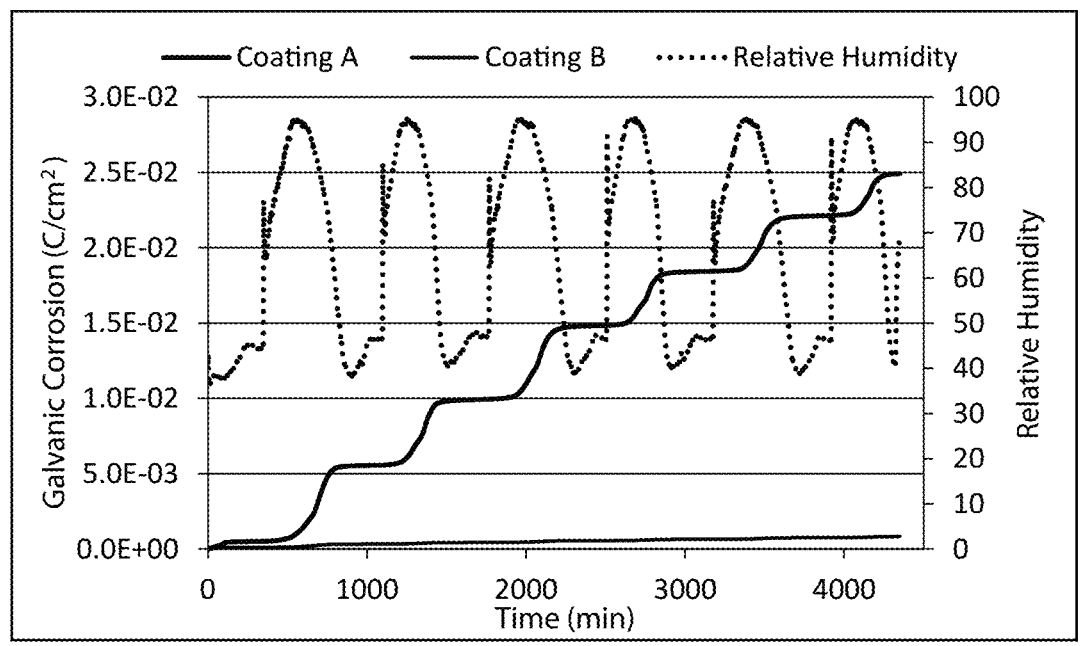
FIG. 8 shows a plot of an example time-based cumulative galvanic corrosion for aluminum/copper galvanic corrosion sensors with coatings tested in an accelerated corrosion test along with a plot of an environmental parameter of relative humidity.

FIG. 8 shows a plot of an example time-based cumulative galvanic corrosion for aluminum/copper galvanic corrosion sensors with coatings tested in an accelerated corrosion test along with a plot of an environmental parameter of relative humidity.

Figure 9:
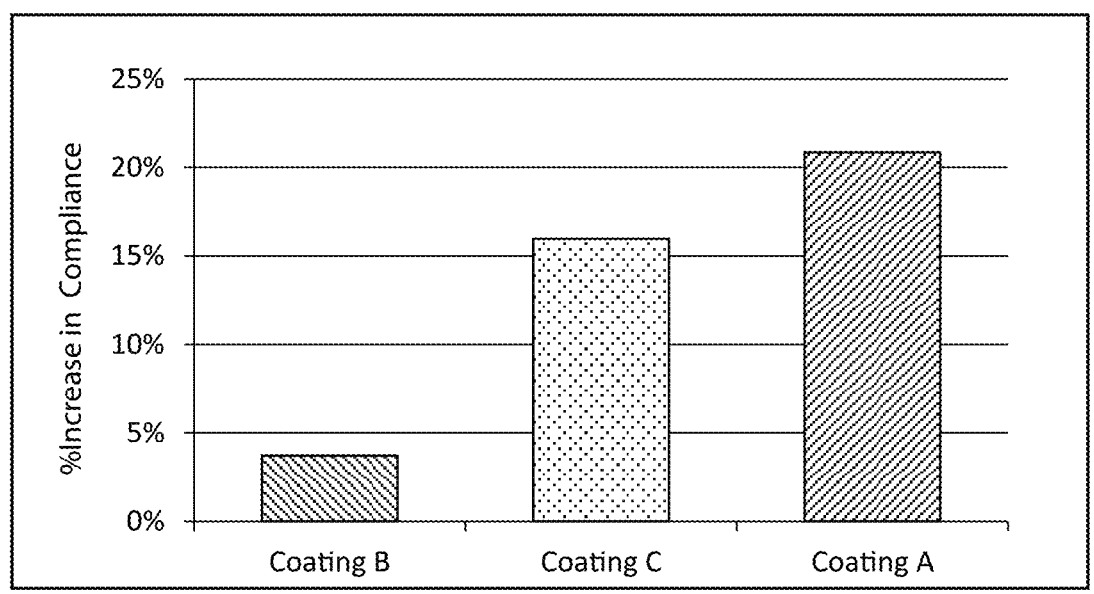
FIG. 9 shows an example of a change in compliance of a mechanical test specimen with three different coatings tested after exposure to a corrosive environment.

FIG. 9 shows an example of a change in compliance of a mechanical test specimen with three different coatings tested after exposure to a corrosive environment.

The multi-sensor panel 16 of the corrosion and coating test system 10 for quantifying coating performance includes individual sensor elements for measuring various corrosion phenomena including free corrosion, galvanic corrosion, and coating barrier properties. Non-limiting examples of such sensors are shown in FIGS. 10 and 11a-11f. Some of these sensors are described in PCT/US2013/050424, the contents of which is incorporated herein by reference.

Figure 10:
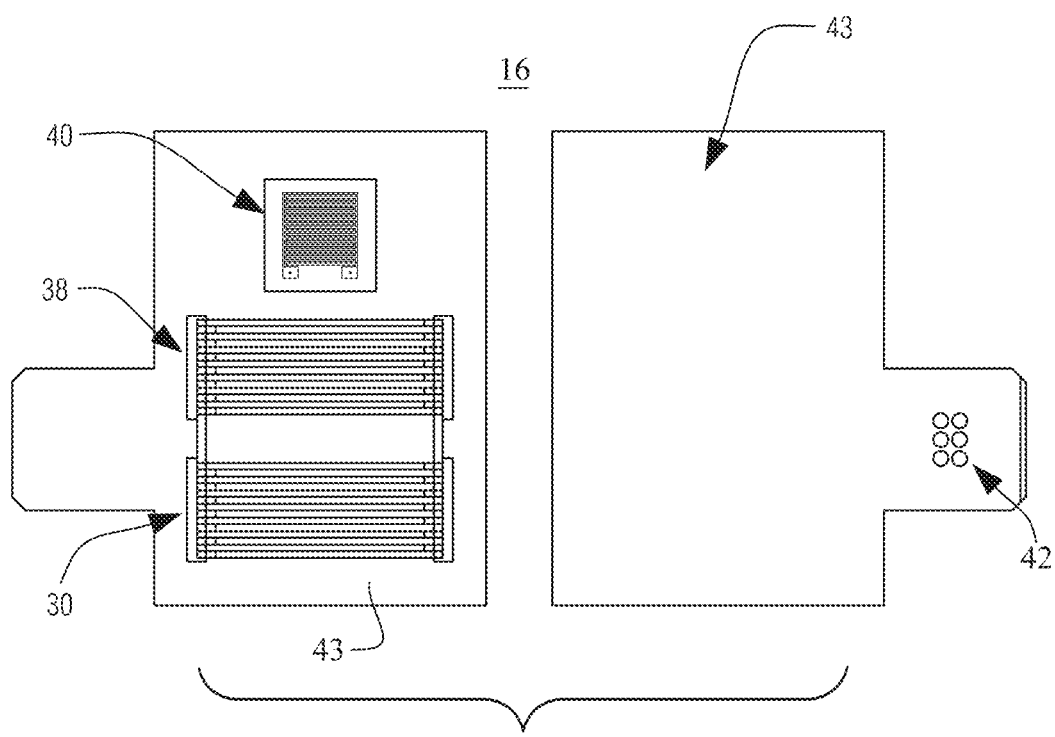
FIG. 10 shows a non-limiting embodiment of an example multi-sensor panel used on instrumented test rack shown in FIG. 2.

The multi-sensor panel 16 of the non-limiting example shown in FIG. 10 includes a mounted array that includes a free corrosion sensor 38, galvanic corrosion sensor 30, and coating barrier property sensor 40. These elements can be fastened or bonded to a support panel 43 that contains the electrical interconnections and electrical contacts 42 between the sensors and instrumented test rack. The support panel 43 enables processing of the multi-sensor panel through cleaning, pretreatment, coating application, and curing steps for preparing the coating system and materials to be tested. The support panel 43 protects the sensor electrical interconnects from the test environment and has means for electrically connecting to the instrumented test rack 12. The electrical contacts 42 are protected during the coating process using tape or other removable masking and are designed to be protected from the severe environment during testing by the support panel 43 and electrical interface 48. The multi-sensor panel 16 can be used either as a onetime use item that is disposed of after each environmental test, or provide means for restoration of the sensing elements after each test.

The multi-sensor panel 16 may also support environmental sensors of air temperature and relative humidity 17b, surface temperature 17a, and conductivity 34 in addition to the free corrosion sensor 38, galvanic corrosion sensor 30, coating barrier property sensor 40. The environmental sensors may also be mounted on the electronics enclosure 15 as shown in FIG. 1 and FIG. 2. It is understood that by placing a non-conductive material on the free corrosion sensor 38 or galvanic corrosion sensor 30 that crevice corrosion processes can be monitored.

Figure 11A:
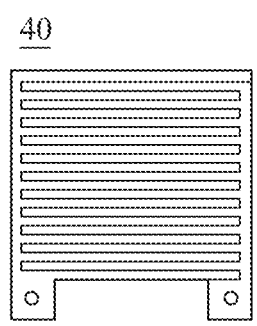
FIGS. 11a-11f show example sensors that may be included on the example multi-sensor panel including coating barrier property, free corrosion, and galvanic corrosion sensors.
Figure 11B:
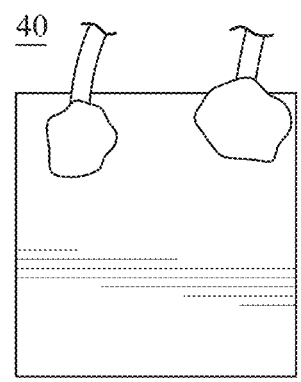
Figure 11C:
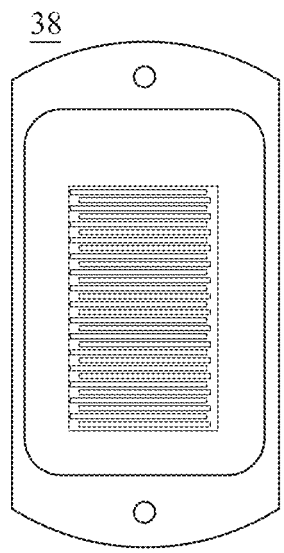
Figure 11D:
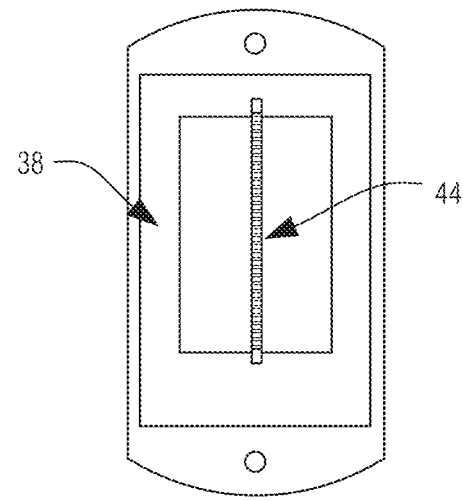

FIGS. 11c and FIG. 11d show non-limiting example free corrosion sensors 38 that may be fabricated from standard reference materials or alloys of interest for a specific application are used to evaluate protective properties of coatings. The sensors are either fully coated or coated with a controlled coating defect 44. During testing electrochemical or electrical resistance, or electromagnetic induction measurements can be used to quantify the corrosion rate shown in FIG. 5 or cumulative corrosion shown in FIG. 7 during the environmental testing. The free corrosion sensor 38 can be used for measuring crevice corrosion by overlaying all or part of the sensor with a material that forms an occluded cell. The crevice gap may be controlled using a shim or spacer of known thickness to separate the crevice former material from the sensing element.

Free corrosion rate sensors 38 may include interdigitated electrodes formed by thin film metallization and patterning, foil lamination and patterning, or laminate layers and sectioning methods. In the case of laminate-layered free corrosion sensors 38, preferred metallurgical orientations can be established. Interdigitated free corrosion sensors 38 may be excited using low voltage, less than 100 mV, AC or other time dependent waveforms and direct measurements of current to obtain impedance across the electrodes. The measured currents can be used directly as measures of the rate of charge passed by corrosion, or the impedance can be used to estimate the corrosion current using the Stern-Geary relationship and polarization resistance methods.

In the case of two electrode measurements, two electrodes of the same alloy are used to obtain corrosion rate measurements using traditional techniques of linear polarization resistance or electrochemical impedance spectroscopy (EIS) to obtain polarization resistance ($R_p$) measurements (ASTM G59). Assuming a value for the Stern-Geary constant ($\beta$), the corrosion rate ($i_{corr}$) can be calculated using the Stern-Geary equation:

$$R_p = \frac{\beta}{I_{corr}}; \text{ or } i_{corr} = \frac{\beta}{R_p * A} \quad (1)$$

where $I_{corr}$ is the measured current, and A is the electrode area.

$$\beta = \frac{b_a b_c}{2.3(b_a + b_c)} \quad (2)$$

where $b_a$ and $b_c$ are the anodic and cathodic Tafel slopes.

$$Z_{\omega \to 0} = 2R_p + R_s, \text{ and } Z_{\omega \to \infty} = R_s \quad (3)$$

$$R_p = \frac{Z_{\omega \to 0} - R_s}{2}; \text{ or } R_p = \frac{Z_{\omega \to 0}}{2} \quad (4)$$
assuming $R_p \gg R_s$ Two electrode measurements can be made for any alloy of interest such as steel or aluminum that is configured into a parallel plate or interdigitated electrodes. From time based measurements of corrosion rate, the cumulative corrosion is obtained using Faraday's Law (Equation 5) and integrating the mass loss rates over a given exposure time.

$$MR = \frac{i_{corr}}{F} \frac{MW}{z} \quad (5)$$

where MW is the molar mass of the alloy, z is the valence of ionic species produced by corrosion, and F is Faraday's constant.

Free corrosion can also be assessed by measurements of cumulative corrosion using electrical resistance sensors (not shown) typically fabricated from thin metal inlays on circuit boards. As the inlay corrodes, the resistance changes, and this resistance can be used to quantify material loss. These sensors often incorporate bridge circuits for comparative measurements of resistance change and temperature compensation. Electromagnetic induction or eddy current impedance measurements similarly can be used for assessing corrosion damage. For both types of cumulative corrosion measurements, an estimate of corrosion rate can be made by taking the derivative of the cumulative corrosion damage measurement as a function of time.

Figure 11E:
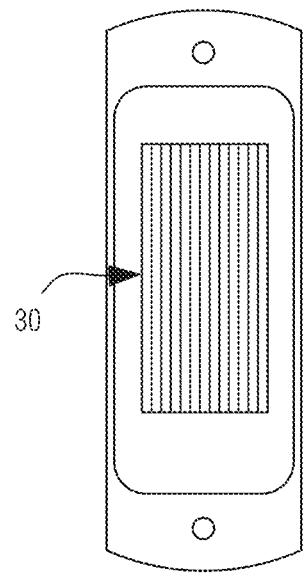
Figure 11F:
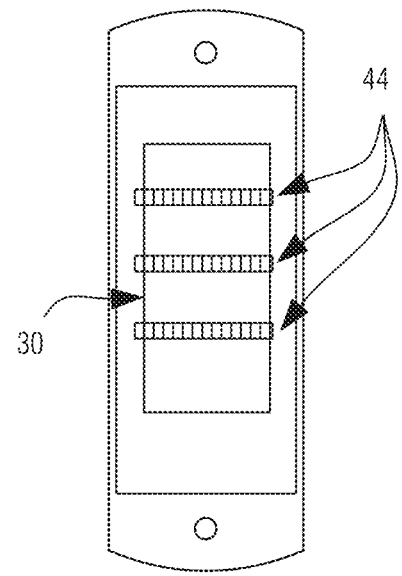

FIG. 11e and FIG. 11f show non-limiting example Galvanic corrosion sensors 30 including two or more dissimilar alloys or conductive materials separated by a dielectric material. These alloys can be selected based on standard reference materials or based on the materials used in the intended application. In either case, dissimilar metals or composite materials may have differences in electronegativity that result in polarization that produces galvanic current between the electrodes when electrically shorted in the presence of an electrolyte. The galvanic current can be measured by either a zero resistance ammeter or using a known resistance between the electrodes and measuring the voltage to obtain current between the materials of the galvanic couple. As with the free corrosion sensor 38, the galvanic corrosion rate sensors 30 are either fully coated or coated with a controlled coating defect 44.

Galvanic corrosion sensors 30 may include interdigitated electrodes of different metals, alloys, or composites formed by thin film metallization and patterning, foil lamination and patterning, or laminate layers and sectioning methods. In the case of laminate-layered galvanic corrosion sensors, preferred (but example) metallurgical orientations can be established. The ratio of electrode areas can be tailored to control the severity of the galvanic couple. The galvanic corrosion rate can be used to estimate material mass loss using Faraday's Law (Equation 5). Galvanic corrosion sensors 30 can be used for quantifying cumulative corrosion damage that is estimated by applying Faraday's Law (Equation 5) and integrating the galvanic corrosion rate data as a function of time. FIGS. 6 and 8 show an example of galvanic corrosion rate and cumulative corrosion as function of time obtained using galvanic corrosion sensors 30 with coating defects 44 for two different coatings. The galvanic corrosion sensor 30 can be used for measuring crevice corrosion by overlaying all or part of the sensor with a material to form an occluded cell. The crevice gap may be controlled using a shim or spacer of known thickness to separate the crevice former material from the sensing element.

Galvanic corrosion sensors 30, free corrosion sensors 38, and crevice forming materials can be combined in a variety of forms to measure the influence and coupling of boldly exposed areas with crevice areas, and measuring the effect of concentration cells such as the formation and strength of oxygen concentration cells. Similarly, if the electrodes are strained, or otherwise loaded, current transients and the precursor, incubation, and growth processes for environment assisted cracking can be measured.

FIGS. 11a and 11b show an example coating barrier property sensor 40 that measure the capacity of a coating or coating system to resist the penetration of moisture or other corrosives through a nominally intact coating. Measurements of the barrier properties can be accomplished with any interdigitated metallic electrodes such as described above for the free corrosion sensor 38, galvanic corrosion sensor 30, or preferably a noble metal interdigitated electrode sensor shown in FIG. 11a and FIG. 11b. Low amplitude excitation signals, e.g., below 100 mV, are preferably used to obtain coating impedance measurements. An example impedance spectrum can be used to assess coating barrier properties from 0.01 Hz to 500 kHz. Preferably, barrier property measurements are made using an intermediate to higher frequency in the example range of 1 kHz to 100 kHz with electrochemical impedance spectroscopy methods. Frequency measurements in this example range tend to be more sensitive to the coating barrier properties and less dependent on electrochemical reactions at the surfaces of the metal sensing elements.

As part of the multi-sensor panel 16 or instrumented test rack 12, environmental sensors may also be used to verify exposure conditions. These environmental measurements may include relative humidity and air temperature sensors 17b, and panel surface temperature sensors 17a. These sensors may include embedded RTD's, thermocouples, and combined temperature and humidity sensors. Other chemical or environmental sensors may be used for detecting oxygen, chloride, sulfur, nitrogen, ozone or any chemicals, gases, and compounds that may be relevant for a particular environment or application. Environmental sensors may also include measurement of light and radiation such as infrared and ultraviolet radiation intensity.

The instrumented test rack 12 may, in an example embodiment, accommodate mechanical test specimens 18 for use in establishing the ability of coatings to protect materials from corrosion processes that adversely impact the mechanical properties of structures and components. Non-limiting example mechanical test specimens 18 are shown in FIGS. 12a-12c. These mechanical test specimens 18 may have a wide range of geometries that include simple dog bone tensile samples or four point bend samples (ISO 11782-1 and 11782-2). In a simple embodiment, the mechanical test specimens shown in non-limiting example FIG. 12a are coated, without or with simulated defects 44, and exposed for the duration of the accelerated test. At the conclusion of a corrosion test, the samples are mechanical tested for standard mechanical properties, such as compliance shown in FIG. 9, or residual yield and ultimate tensile strength. The samples could also be tested to determine fatigue resistance properties, such as cycles to crack initiation, cycles to failure, or equivalent initial flaw size. Damage morphology and total corrosion damage to the mechanical test specimens can also be characterize by microscopy and metallographic techniques.

The instrumented test rack 12 may support a mechanical test assembly 13 that provides a mechanism to apply static mechanical loads to the fracture samples in situ during an exposure test. A non-limiting example is shown in FIGS. 12b and 12c where the load is transmitted to the mechanical test specimen 18 through the load pins 46 that contact the specimen in a four-point bend geometry. By compressing the two pairs of load pins 46 on either side of the mechanical test specimen 18, a bending moment is produced in the center section that stresses the mechanical test specimen 18. Mechanical test specimen 18 loading, by example, may be accomplished by mechanical actuation using dead load weights, spring, screw, hydraulic, piezoelectric, and/or pneumatic actuation methods. The mechanical test assembly 13 may apply a range of loading modes to mechanical test specimen 18 including tensile or bending to produce Mode I type crack tip opening displacement, but other crack opening modes or mixed modes may be used.

Sample loading may be by constant displacement or constant loading, where measures of load and/or displacement can be used to track in situ failure processes or crack growth rates of environment-assisted cracking due to the simultaneous action of environment and mechanical loading as described for example in U.S. Pat. No. 8,499,643, the contents of which are incorporated herein by reference. Displacement and load may be detected as example by linear variable differential transformer, inductive position sensors, strain gage based load cells, and hydraulic or pneumatic pressure gages. Methods for monitoring crack growth rates include optical inspection, electrical potential drop, ultrasonic, or eddy current techniques.

Another non-limiting example embodiment provides a mechanical test assembly 13 capable of dynamic load actuation of the mechanical test specimen 18 to induce environment-assisted cracking and corrosion fatigue fracture. As an example shown in FIG. 12b, load is transmitted to the specimen through the load pins 46 that contact the specimen in a four-point bend geometry. By varying the compression load between the two pairs of load pins 46 on either side of the mechanical test specimen 18 a fatigue load can be produced. Mechanical test specimen 18 loading may be accomplished for example by mechanical actuation using hydraulic, piezoelectric, and/or pneumatic actuation methods. The mechanical test assembly 13 may apply a range of loading modes to mechanical test specimen 18 including tensile or bending to produce Mode I type crack tip opening displacement, but other crack opening modes or mixed modes may be used.

A dynamically-actuated mechanical test assembly 13 may include load and displacement measurement to estimate crack growth rates and evaluate sample compliance as a function of time throughout the exposure test. Other potential methods for monitoring crack growth rates include optical inspection, electrical potential drop, ultrasonic, or eddy current techniques. Parameters of interest that may be used to assess the corrosion fatigue performance include initiation time, threshold stress intensity, cycles to failure, or corrosion modified equivalent initial flaw size. Other techniques and/or mechanisms may be used to excite damage to the mechanical test specimens including application of electrochemical potential, galvanic coupling, or formation of crevices.

Besides the multi-sensor panel 16 and mechanical test specimen 18, the instrumented test rack 12 may in non-limiting example embodiments also support standard test panels 14, mass loss coupons 19, and/or environmental sensors 17a and 17b.

As shown in the non-limiting example in FIG. 4, the electronics enclosure 15 contains an electronics module 24 that interfaces with the sensors of the multi-sensor panels 16. The instrumented test rack 12 physically supports the electronics enclosure 15 along with the other items already described above. The electronics module 24 serves as the data acquisition and control system for the multi-sensor panels 16 on the instrumented test rack 12 (see PCT/US2013/050424 for an example battery-powered data acquisition and control system). Furthermore, the electronics module 24 also includes a communications interface between the instrumented test rack 12 and base station 22. The electronics enclosure 15 containing the electronics module 24 provides electrical connectors to the sensors of the multisensor panels 16. The electronics enclosure 15 protects the electronics module 24 from harsh exposure environments.

As already explained, the architecture of the instrumented test rack 12 can support a variable number of multi-sensor panels 16, environmental sensors 17a and 17b, standard test panels 14, and mechanical test specimens 18. By way of example only, an instrumented test rack 12 might support one to three sets of panels 16 and specimens 14 and 18. Multiple instrumented test racks, e.g., 12a and 12b, can be used and monitored simultaneously by the base station 22 using a wired or wireless digital multi-drop communications bus. The sensor data acquisition system includes instrumented test racks 12 for sensor interfacing, communications bus between the instrumented test rack and base station 22, and a base station 22 or central network user interface for system setup, control, data processing, display, and storage. Hardware, embedded firmware, and data processing methods currently used for corrosion monitoring, based on the IEEE 1451 family of standards for plug-and-play functionality of a distributed sensor network are appropriate for the corrosion and coating evaluation system application (see for example PCT/US2013/050424 incorporated by reference above). The instrumented test rack 12 may be powered by battery or wired power from an external source.

The packaging and electronics hardware design approach of the corrosion and coating evaluation system is preferably (though not necessarily) modular. In a non-limiting example embodiment shown in FIG. 13, whereby different functional aspects of the instrumented test rack 12 can be implemented and supported with modular electronic components as part of the electronics module 24. The three components of the electronics module 24 of the instrumented test rack 12 are the baseboard 46, communications interface 28, and analog interface board 26, and power supply 52 (see for example PCT/US2013/050424). The analog interface board 26 supports the excitation and signal conditioning needed for the multi-sensor panels 16, mechanical test assembly 13, and environmental sensors 17a and 17b. The analog board 26 will interface between the sensors and the baseboard 46 electronics. The baseboard 46 technology used for PCT/US2013/050424 is one example that may be used for the corrosion and coating evaluation system. A preferred example of a communications interface 28 between the base station 22 and instrumented test rack 12 is a wireless IEEE 802.15.4-2003 ZigBee module, but other wireless and wired interfaces may be used, such as WiFi or RS-485 data bus.

Figure 13:
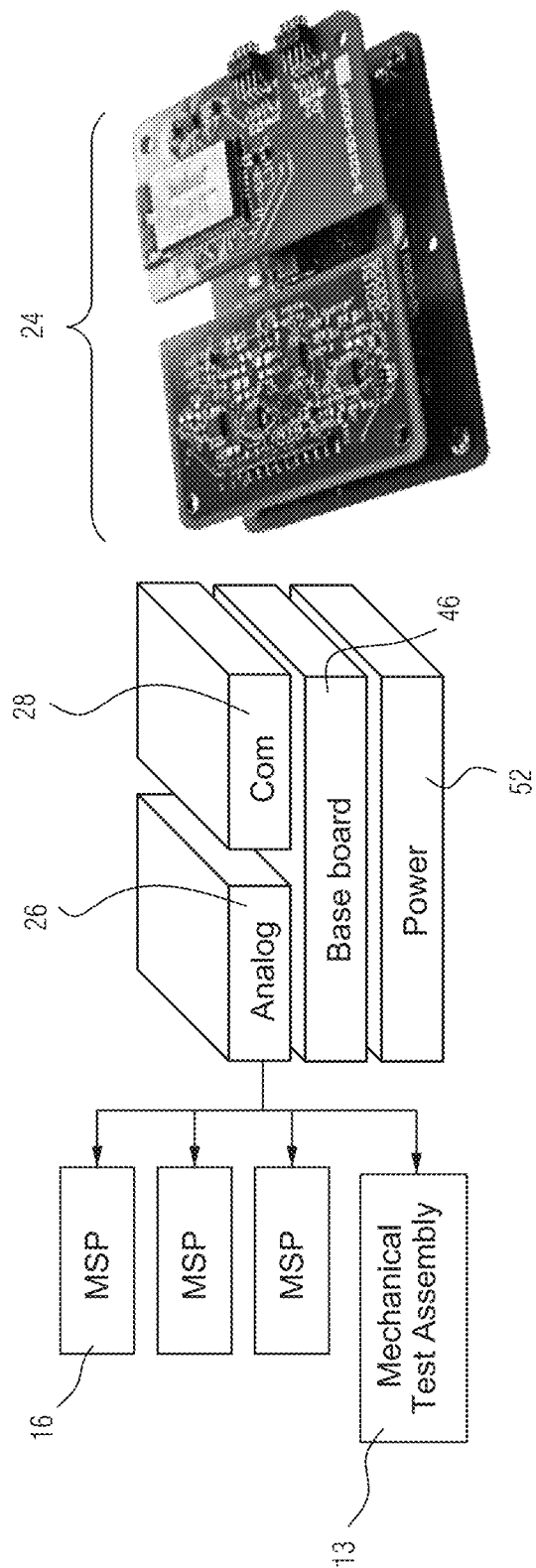
FIG. 13 shows a further depiction of an example embodiment of an electronics module useable with the multi-sensor panels and instrumented test rack.

The non-limiting example embodiment for a radio-based electronic module 24 shown FIG. 13 includes an analog and digital interface board 26, baseboard 46, communications board 28, and a power source 52. The baseboard 46 incorporates two connectors: a first for the communications board 28 and a second for the analog interface board 26. The first connector passes communications signals over a Serial Peripheral Interface (SPI) bus, for example, and various universal asynchronous receiver/transmitter (UART) lines. Additionally, the first connector passes various digital I/O lines to the communications board that can be used as hardware interrupts to initiate wake-up events based on communications activities. The analog interface connector provides access to a baseboard microcontroller via analog to digital converter pins, thus allowing measurements to be made from various analog sensors. The connector also provides access to various digital I/O lines, and like the communications board interface, provides access to hardware interrupt lines. These external interrupt lines can be used to initiate wake-up events based on sensor outputs.

Embedded firmware within the electronics module 24 on the baseboard 46 performs several functions including: 1) system operations and interface with the base station 22, 2) system power efficiency, and 3) embedded algorithm execution. Each firmware component functions in concert to provide an embedded system that collects, processes, and transmits the multi-sensor panel 16, environmental sensors 17a and 17b, and mechanical property data from the mechanical test assembly 13.

The electronics module 24 preferably schedules measurements, stores data, processes data, and communicates pertinent information between instrumented test racks 12 and the base station 22. The firmware preferably allows the system to schedule a number of events, such as waking up based on internal alarms from the real time clock, synchronizing time events, and schedule based communications. In one example embodiment, the system includes a defined set of operations for execution that involve appropriate circuitry communicating with on-microcontroller peripherals such as analog to digital converter, communicating with off-microcontroller peripherals such as flash memory or communications modules, and initiating network-wide data transfers.

In example embodiments, many functions in the instrumented test rack 12 electronics module 24 can be handled using an embedded operating system such as a real time operating system (RTOS). A RTOS can have a small memory footprint for use in low power embedded applications but also allows for efficient handling of function scheduling and execution. Use of an operating system such as RTOS simplifies the overall development efforts related to efficient operations of embedded systems.

The electronics module 24 for each instrumented test rack 12 also preferably stores specific information related to sensors and materials being used with the rack for any given exposure test. The instrumented test racks 12 and corrosion and coating evaluation system may be compliant with the IEEE-1451 standards for smart sensor design. These standards may be implemented through firmware that allows for efficient transfer of the IEEE-1451 defined Transducer Electronic Data Sheets (TEDS) between the instrumented test racks 12 and base station 22. The TEDS will be defined during setup of the instrumented test rack 12 prior to starting an exposure test. The instrumented test rack 12 will be able to store pertinent attributes regarding the types of sensor elements and associated test specific information for the individual test rack 12. This allows for ease of operation of the instrumented test racks 12, configuration of the multi-sensor panels 16 for individual tests, addition and removal of test articles (instrumented test racks 12, multi-sensor panels 16, mechanical test specimens 18, standard test panels 14) during the test, and removing and replacing items supported by the instrumented test rack 12.

When the instrumented test racks 12 are used with wireless interfaces, ultra-low power operation and power management is supported by the electronic hardware design and firmware operation. The embedded firmware system manages the periodic measurement of the multi-sensor panels 16, environmental sensors 17a and 17b, and mechanical test specimen. Data rates and wireless communications are user selectable using the base station 22 user interface during test setup and may be modified during an exposure test. The data transfer from the instrumented test rack 12 to the base station 22 can happen at longer intervals further reducing the power consumption associated with wireless data transmission. The wireless instrumented test rack 12 may be battery powered, but line power could also be used. It is also possible that for outdoor exposure sites power will be harvested, supplied, and stored using other external means such as solar panels and capacitors. For battery powered operation, electronics module 24 may include automated monitoring of battery charge so that low battery conditions can be addressed prior to loss of operation and data. The instrumented test rack 12, electronic enclosure 15, and electronics module 24 design includes means for recharging and/or replacing the batteries without interrupting operation.

The electronics module 24 may also have firmware for processing sensor data. It is understood that data processing may occur on the instrumented test rack 12 or base station 22. Some level of power efficiency can be achieved when processing data on the instrumented test rack 12. Also, embedded built-in-tests for verifying proper system operation can improve the reliability of the system along with generation of automated alerts for operators.

A variety of types of communications boards 28, depending on the type of communications used, may be employed in example embodiments. For wired communications between the instrumented test racks 12 and base station 22, a pass through from the baseboard 46 to the communications board 28 could be sufficient, as hardware required for RS-485 or Ethernet communications may be incorporated on the baseboard. For wireless communications, hardware required to implement various wireless communications protocols may be provided on the communications board 28. These wireless communications include Wi-Fi (IEEE 802.11), cellular, satellite, and Zigbee® (IEEE 802.15.4) communications. For one example embodiment, a Meshnetics ZigBit™ Zigbee® communications module may be included on the communications board 22, along with various power control circuits and a temperature sensing IC. The communications board 22 is designed using a connector for attachment of an external antenna. This allows for tailoring of the antenna without modification to any other part of the system, should an external antenna be required.

Figure 14:
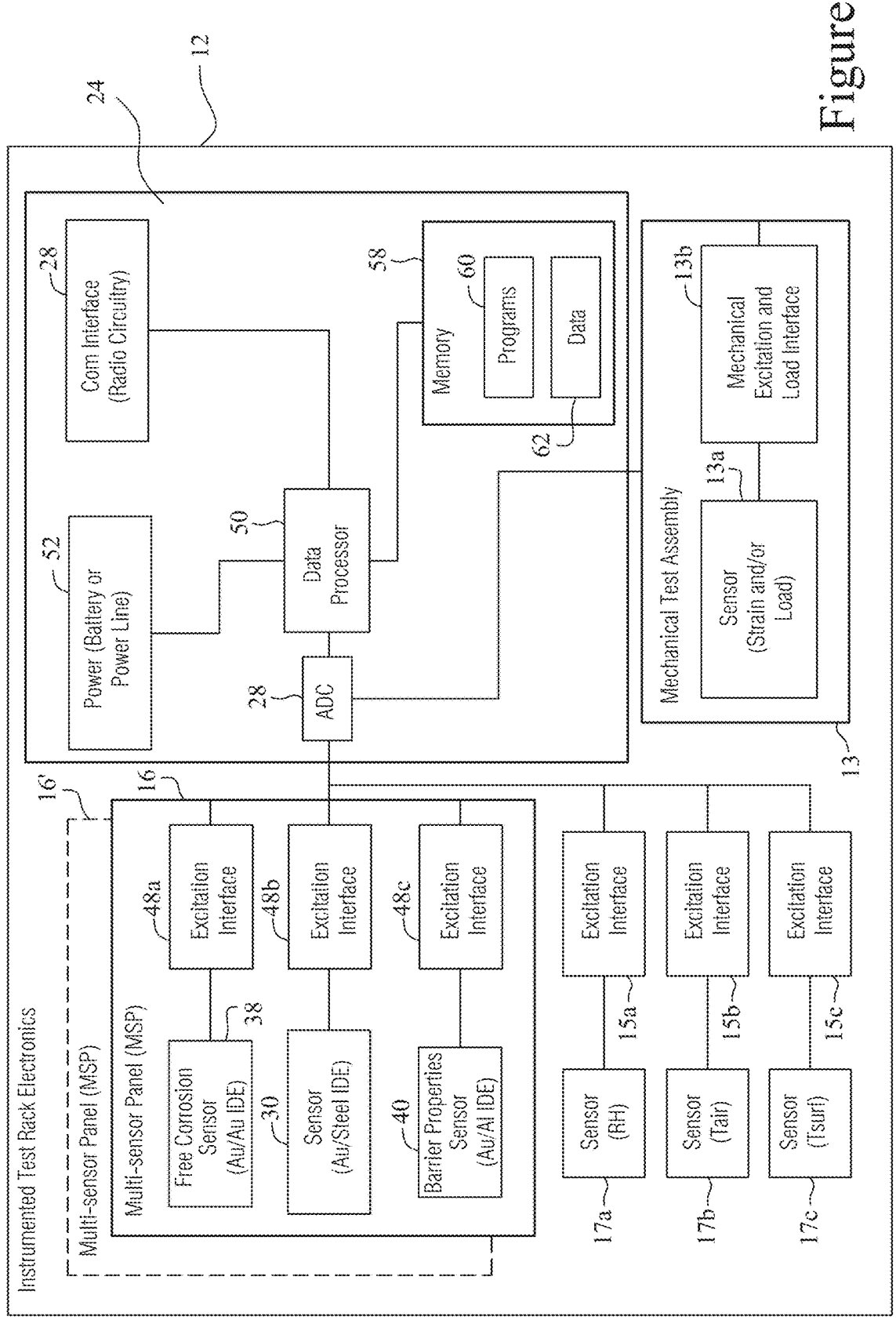
FIG. 14 is a functional block diagram illustrating a non-limiting example embodiment of electronics useable with the instrumented test rack shown in FIG. 2.

FIG. 14 is a functional block diagram illustrating a non-limiting example embodiment of electronics useable with the instrumented test rack shown in FIG. 2. The instrumented test rack 12 with the electronics enclosure 15 provides the physical and electrical interfaces. The electronics module 24 in the electronics enclosure 15 performs automated control and operation throughout a test including sensor excitation, signal conditioning, data processing, and temporary information storage prior to communication with the base station. The electronics module 24 provides an analog to digital converter 28 and analog or digital excitation and acquisition interfaces 48a-48c, 15a-15c, 13a and 13b for all the sensing elements on the multi-sensor panel 16, environmental sensors 17a and 17b (combined RH and air temperature), and mechanical test assembly 13. Analog sensor signals are converted to digital signals for processing using program software 60 stored in memory 58 and executed by the data processor 50. The data processor 50 also controls the acquisition timing, sensor data storage 62 within the instrumented test rack memory 58, and periodic sensor data down load and communication with the base station 22 via the communications interface 28. Circuitry for power management is also included within the instrumented test rack when running on battery or line power 52.

Figure 15:
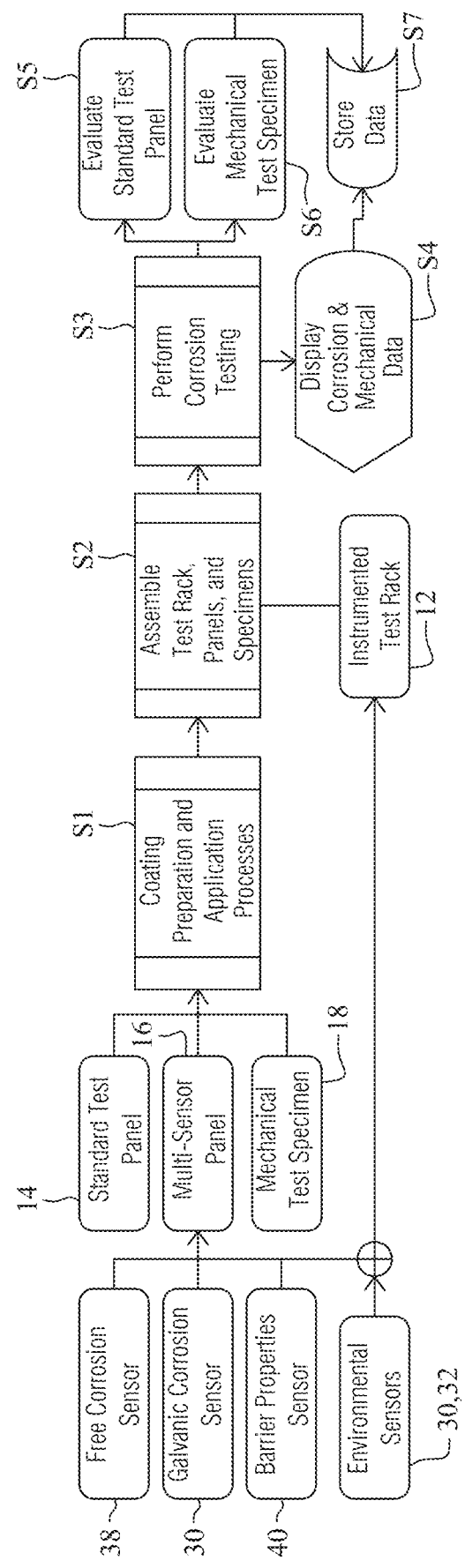
FIG. 15 is a flow diagram illustrating various example processes to prepare, assemble, and operate an instrumented test rack to perform corrosion and coating evaluation.

FIG. 15 is a flow diagram illustrating various example processes to prepare, assemble and operate an instrumented test rack to perform corrosion and coating evaluation. Prior to assembly of the instrumented test rack 12, the standard test panel 14, multi-sensor panel 16 with free corrosion sensor 38, galvanic corrosion sensor 30, and barrier property sensor 40, and mechanical test specimen 18 are all processed (step S1) according to specifications for the coating system to be tested. The standard test panels 14 are preferably produced according to industry specifications. The mechanical test specimens 18 are fabricated based on a desired measurement of cracking or mechanical property testing. The multi-sensor panel 16, standard test panel 14, and mechanical test specimen 18 are then prepared for coating, which may include any combination of cleaning and pretreatment as part of the coating process. The coatings are applied, which may be any type of coating to be evaluated and application by example may be brush, spray, or dip applied. The mechanical test specimens 18 and galvanic 30 and free corrosion 38 sensors may optionally have artificial coating defects, and the standard test panels 14 may be scribed or impacted after coating.

Once the coating application is complete, the coated multi-sensor panel 16, standard test panel 14, mechanical test specimen 18 are assembled (step S2) on the instrumented test rack 12 with environment sensors 17a and 17b and placed in the accelerated corrosion test chamber 20 to perform the testing (step S3). The instrumented test rack 12 physically supports the test items and provides electrical connections to the sensors of the multi-sensor panel 16 and mechanical test assembly 13. Environmental sensors 17a and 17b for temperature and relative humidity may be included on the instrumented test rack 12 or multi-sensor panel 16.

The test environment may, for example, be an accelerated corrosion test chamber, outdoor exposure site, or service environment. During the test, real time displays (step S4) of test conditions, corrosion rates, and cumulative corrosion are output at the base station. Example time based plots for relative humidity, and the rate and cumulative data for free corrosion and galvanic corrosion are shown in FIGS. 5-8. During the test, mechanical test specimens 18 and standard test panels 14 can be removed for evaluation and rating as shown in FIG. 9. Once the test is concluded, the standard panels 14 are rated (step S5) the mechanical test specimens 18 evaluated (step S6) and all the data is stored (step S7). When the mechanical test assembly 13 used includes load and displacement data, this data would also be processed, displayed (step S4), and stored (step S7).

FIG. 16 is a non-limiting flowchart illustrating example of procedures that may be carried out using two or more instrumented test racks 12 for determining protective properties and performance of coatings A and B tested in an accelerated corrosion test chamber 20, outdoor exposure site, or collocated with a structure of interest. Each instrumented test rack 12 with environmental sensors 17a and 17b, multi-sensor panels 16, and mechanical test assembly 13 measures the protective properties of the coating. The multisensor panels 16 and mechanical test specimens 18 are coated with Coating A that has no corrosion inhibitor and Coating B that has corrosion inhibitor and then place on the instrumented test racks 12. The instrumented test racks 12 of FIG. 3 are placed in an environment of interest, such as an accelerated corrosion test chamber 20.

The instrumented test rack 12 makes periodic measurements S10 of environmental parameters, free corrosion, galvanic corrosion, and barrier properties using the multi-sensor panels 16 with Coating A and Coating B are collected and processed S12. Periodicity of these sensor measurements may range from seconds to minutes or hours. The sampling rate is determined based on how quickly environmental conditions change and the total expected duration of the test. For accelerated laboratory, samples may be collected every one to ten minutes. For outdoor testing, data collection may occur every five minutes to one hour. The data from the multi-sensor panel 16 may be stored on the instrumented test rack 12 and then downloaded periodically or on demand to the base station 22, or processed and stored on the instrumented task rack 12 prior to transmission to the base station 22. The free corrosion and galvanic corrosion rate data from the multisensor panel 16 can be integrated over each sampling interval to obtain the cumulative mass loss by free corrosion or galvanic corrosion S14. The performance of Coating A and Coating B can be compared at any point during a test or at the conclusion test as shown in FIGS. 5-8. The parameters that can be used to compare coatings are average and maximum free corrosion rate and galvanic corrosion rate, total free corrosion mass loss, and total galvanic corrosion mass loss, or barrier resistance of the coating. The environmental data of relative humidity and temperature for each instrumented test rack 12 are used to make sure that the test conditions for Coating A and Coating B are similar S22. For tests with similar conditions, the above multi sensor panel 16 measurement parameters can be used to compare the performance S24 of Coating A and Coating B for product selection S27. The measurement system can be used to compare more than two coatings simultaneously, and comparisons can be made between coatings run at different times if the test conditions are similar.

The instrumented test rack 12 may include the mechanical test assembly 13. For the non-limiting example of FIG. 16, the mechanical test specimens 18 with Coating A and Coating B are tested with mechanical test assemblies 13 that can stress the specimens while exposed to aggressive environments. The mechanical test assembly 13 can apply constant load, constant displacement, or dynamic stressing under load control or displacement control to evaluate the environment-assisted cracking of a mechanical test specimen 18. The instrumented test rack 12 makes periodic measurements S10 of load and displacement for the mechanical test specimen with Coating A and Coating B. These measurements can be high frequency on the order of hundreds to thousands of samples per second for feedback control of load and displacement in static and dynamic testing. Load and displacement data can be used to estimate crack length S16 using compliance calibration curves derived experimentally and using finite element analysis. The load and displacement data from mechanical test assembly 13 may be stored on the instrumented test rack and then downloaded periodically or on demand to the base station, or processed and stored on the instrumented task rack prior to transmission to the base station.

For static load or displacement testing, the derivative of the crack length versus time can be use used to calculate the crack velocity S18. Using fracture mechanics analysis of the mechanical test specimen 18, crack velocity versus stress intensity plots are obtained S20 for quantifying the influence of Coating A and Coating B on environment-assisted cracking S26. The parameters that can be used to compare coatings for effect on environment assisted cracking are threshold stress intensity and crack velocity for a given stress intensity.

Similarly, for fatigue testing velocity can be expressed as change in crack length per cycle (da/dN). The effect of Coating A and Coating B on corrosion fatigue performance can be quantified by cycles to failure, or parameters derived from the measured da/dN curves such as threshold stress intensity, and da/dN at given stress intensities, or parameters obtained from fitting the data to fatigue crack growth models such as a Paris' law S26. When making coating performance comparisons S27, the environmental data of relative humidity and temperature for each test rack are used to make sure that the test conditions for each coating are similar S22.

Although the above example in FIG. 16 may have much of the sensor data processing being performed locally at each instrumented test rack 12, alternative example embodiments may have the raw data communicated to the base station 22 for processing. The base station 22 receives from each instrumented test rack the environmental 17a and 17b, multi-sensor panel 16, and mechanical test assembly data 13. That data is then used to determine free corrosion and galvanic corrosion rates, associated cumulative corrosion, and crack parameters from the compliance model of the mechanical test specimen. The comparison of Coating A and B is done on the base station using the coating performance parameters extracted from the free corrosion, galvanic corrosion, and mechanical test measurements.

The use of standard calibration multi-sensor panels 16, environmental sensors 17a and 17b, and load and displacement gages with the instrumented test rack 12 provide a means to periodically verify and calibrate proper corrosion and coating evaluation system operation. In another non-limiting example embodiment, the instrumented test rack 12 is designed to also physically support standard test panels 14 used for paint qualifications according to military or industry standards. See the example in FIG. 2. Standard test panels 14 typically are flat sheet or plates fabricated from a reference alloy or alloy specific to an application. The panels are coated and often damaged by scribing or machining prior to exposure testing. The instrumented test rack 12 provides the means to collocate a number of standard test panels 14 (1-5 panels) with the multi-sensor panels 16, and it holds samples in the proper orientation during testing. After a given period of time or at the conclusion of an exposure test, the standard test panels 14 are removed and rated for damage using well known standardized methods (ASTM D1654, ASTM G1). The standard test panel 14 performance data would be entered into the base station 22 software as part of the test report generation. The use of standard test panels 14 supports comparison of the multi-sensor panel 16 data and mechanical test assembly 13 results with historical data.

FIGS. 1 and 4 show a non-limiting example embodiment of the corrosion and coating evaluation system 10 with a user base station 22 that serves as the network interface and system manager to support the extensible number of instrumented test racks 12 being used at any given time. The base station 22 includes network management software for instrumented test rack 12 recognition, test setup and control, and data acquisition. The base station 22 includes computer hardware, network interfaces, and storage devices, along with software for system operation, data processing, display, and recording via a graphical user interface (GUI). The GUI is used for test setup, system calibration, control, and monitoring of the instrumented test rack network through the base station 22. The GUI software will also support data analysis and visualization, data formatting and storage, and standardized test report generation. The system can be used to record and store coating and material information, along with test type, duration, and multi-sensor panel 16 information. At the conclusion of a test, addition information for standard test panel 14 ratings can be entered into the stored exposure test records using a menu accessible through the GUI. The base station 22 may be any computer such as desktop or laptop computer. The base station is used to support the wireless or wired communication with the instrumented test racks 12 via digital multi-drop communications bus using for example a wired RS-485 or wireless interface such as IEEE 802.15.4-2003 ZigBee module. The base station 22 can also provide connectivity to the user network via wired or wireless communication to intranet or internet systems.

The GUI initiates communications with the network of instrumented test racks directly or possibly via a network capable interface (NCAP) or hub device installed on or near an accelerated test chamber 20, collects data from the instrumented test rack 12 network, and graphically presents the multi-sensor panel 16, environmental 17a and 17b, and mechanical property measurements. Additionally, the GUI provides a user with configuration capabilities, such as instrumented test rack 12 measurement frequency, activation and deactivation, instrumented test rack 12 conditions such as coating and test information, and instrumented test rack 12 synchronization. Following hardware deployment, the GUI provides users the ability to completely activate, configure, and observe any element within the network from the base station.

The corrosion and coating evaluation system generates temporal environmental, corrosion, barrier property, mechanical compliance, and residual strength data that can be stored, processed, and reviewed to determine comparative coating and material performance. The data coming from any individual sensor can be processed at the firmware level on the instrumented test rack 12 or by base station 22 software executing on base station data processors. Various software levels can be used by an operator to configure a test, observe operations during a test, run a complete test report, and perform more in-depth analysis. The data sets include time-based arrays of environmental data, corrosion rate, cumulative corrosion, and mechanical properties such as compliance and flaw sized estimates.

Both automated and user initialized fault detection routines can be included at the firmware level on each instrumented test rack 12 and in software executable on the base station 22. Network configuration and the capacity to setup, operate, and swap instrumented test racks 12 and subsystem components during long term testing in multiple accelerated test chambers 20 is accommodated in the hardware and software. User input menus within the GUI are used to automate the record keeping and track individual instrumented test racks 12 with unique identifications and the associated sensor types, materials, test type, and expected test duration. Other user inputs may include but are not limited to include electrode area for calculating current density, sampling intervals, and material properties and property data for mechanical test specimens. The corrosion and coating evaluation system can be used to establish the performance of alloys, alloy combinations, and coatings for predicting performance, comparative testing materials, and qualifying materials for specific uses. The system improves coatings and materials corrosion testing by leveraging advances in sensing and instrumentation to obtain high fidelity data on corrosion performance and degradation processes. The length of qualification processes and the risks associated with material introductions can be reduced due to nature and variety of atmospheric corrosion processes being evaluated. Time based information related to coating breakdown, corrosion initiation, and damage state progression for the various mechanisms are recorded. Atmospheric corrosion rate or rate of change of corrosion can be elucidated; the rank order performance of materials can be obtained at any point throughout the total test period.

Although various embodiments have been shown and described in detail, the claims are not limited to any particular embodiment or example. None of the above description should be read as implying that any particular member, step, range, or function is essential such that it must be included in the claims scope. The scope of patented subject matter is defined only by the claims. The extent of legal protection is defined by the words recited in the allowed claims and their equivalents. All structural and functional equivalents to the members of the above-described preferred embodiment that are known to those of ordinary skill in the art are expressly incorporated herein by reference and are intended to be encompassed by the present claims. Moreover, it is not necessary for a device or method to address each and every problem sought to be solved by the technology described, for it to be encompassed by the present claims. No claim is intended to invoke paragraph 6 of 35 USC § 112 unless the words "means for" or "step for" are used. Furthermore, no embodiment, feature, component, or step in this specification is intended to be dedicated to the public regardless of whether the embodiment, feature, component, or step is recited in the claims.

The invention claimed is:

1. A sensor panel for measuring time varying processes of atmospheric corrosion, comprising:
    multiple sensors configured to measure one or more protective properties of a coating applied to the sensor panel, the sensor panel having at least two different electrochemical sensors from a group of a free corrosion rate sensor, a galvanic corrosion rate sensor, and a coating barrier property sensor, wherein the at least two different electrochemical sensors are each configured to use an electrochemical process to measure the one or more protective properties of the coating applied to the sensor panel, and
    an interface coupled to the sensors and configured to provide measurement signals from the sensors,
    wherein the measurement signals include information relating to one or more protective properties of the coating.

2. The sensor panel in claim 1, wherein each of the sensors comprises plural electrodes and the interface is configured to obtain measurement information from the sensors that is useable to evaluate the one or more protective properties of the coating.

3. The sensor panel in claim 1, wherein the at least two different electrochemical sensors include the free corrosion sensor, and wherein the free corrosion sensor includes interdigitated electrodes.

4. The sensor panel in claim 3, wherein the interdigitated electrodes in contact with the coating are laminated and include a metallographic texture orientation of structural alloys with both surfaces of the electrode sensors being in direct contact with the coating applied to the sensor panel.

5. The sensor panel in claim 3, wherein the coating has a defect of a predetermined geometry that was applied to the coating.

6. The sensor panel in claim 3, wherein the interdigitated electrodes are covered by an inert material to form a crevice to measure free corrosion.

7. The sensor panel in claim 1, wherein the at least two different electrochemical sensors includes the free corrosion rate sensor, and wherein the free corrosion rate sensor is configured to measure free corrosion rate using a current response to a predetermined voltage excitation, and wherein a cumulative corrosion is determinable by integrating the measured free corrosion rate.

8. The sensor panel in claim 1, wherein the at least two different electrochemical sensors includes the free corrosion rate sensor, and wherein the free corrosion rate sensor is configured to estimate free corrosion using polarization resistance.

9. The sensor panel in claim 3, wherein the at least two electrochemical sensors includes the galvanic corrosion rate sensor configured to measure galvanic corrosion using two or more electrodes.

10. The sensor panel in claim 9, wherein an area of each of the electrodes exposed to a corrosive atmosphere is variable.

11. The sensor panel in claim 9, wherein the electrodes are laminated and include a metallographic texture orientation or a composite laminate orientation.

12. The sensor panel in claim 9, wherein the coating has a defect of a predetermined geometry that was applied to the coating.

13. The sensor panel in claim 9, wherein the interdigitated electrodes are covered by an inert material to form a crevice to measure free corrosion.

14. The sensor panel in claim 9, wherein the galvanic corrosion rate sensor is configured to measure a galvanic corrosion rate for each electrode, and wherein a cumulative galvanic corrosion is determinable by integrating the galvanic corrosion rate.

15. The sensor panel in claim 1, wherein the at least two different electrochemical sensors includes the coating barrier property sensor having interdigitated electrodes made using a metal, an alloy, or a noble metal, and wherein the coating barrier property sensor is configured to measure barrier properties of a coating based on impedance measurements between electrodes generated by an excitation voltage.

16. The sensor panel in claim 1, wherein each of the free corrosion rate sensor, galvanic corrosion rate sensor, and coating barrier property sensor is an electrochemical sensor configured to measure, using an electrochemical process, the one or more protective properties of the coating applied to the sensor panel.

17. A method for measuring time varying processes of atmospheric corrosion, comprising:
    using multiple sensors to measure one or more protective properties of a coating applied to a sensor panel, the sensor panel having at least two different electrochemical sensors from a group of a free corrosion rate sensor, a galvanic corrosion rate sensor, and a coating barrier property sensor, wherein the at least two different electrochemical sensors use an electrochemical process to measure the one or more protective properties of the coating applied to the sensor panel, and
    outputting measurement signals from the sensors via an interface on the sensor panel,
    wherein the measurement signals include information relating to one or more protective properties of the coating.

18. The method in claim 17, wherein each of the sensors comprises plural electrodes and the interface obtains and outputs measurement information from sensors that is useable to evaluate the one or more protective properties of the coating.

19. The method in claim 17, wherein the at least two different electrochemical sensors includes the free corrosion sensor, and wherein the free corrosion sensor includes interdigitated electrodes.

20. The method in claim 17, wherein the at least two different electrochemical sensors includes the galvanic corrosion rate sensor configured to measure galvanic corrosion using two or more electrodes.

21. The method in claim 20, wherein the galvanic corrosion rate sensor measures a galvanic corrosion rate for each electrode for determining a cumulative galvanic corrosion.

* * * * *